United States Patent
Bath et al.

(10) Patent No.: US 12,357,787 B2
(45) Date of Patent: Jul. 15, 2025

(54) METHODS OF DETECTING A QUANTITY OF WATER IN A HUMIDIFIER

(71) Applicant: ResMed Pty Ltd, Bella Vista (AU)

(72) Inventors: Andrew Roderick Bath, Sydney (AU); Matthew Rolf Harrington, Sydney (AU); Liam Holley, Sydney (AU); Ronald James Huby, North Epping (AU); Richard Llewelyn Jones, Sydney (AU); Ian Malcolm Smith, Sydney (AU)

(73) Assignee: ResMed Pty Ltd (AU)

( * ) Notice: Subject to any disclaimer, the term of this patent is extended or adjusted under 35 U.S.C. 154(b) by 828 days.

(21) Appl. No.: 16/946,876

(22) Filed: Jul. 9, 2020

(65) Prior Publication Data

US 2020/0338299 A1    Oct. 29, 2020

Related U.S. Application Data

(63) Continuation of application No. 15/030,402, filed as application No. PCT/AU2014/050286 on Oct. 14, 2014, now Pat. No. 10,758,701.

(30) Foreign Application Priority Data

Oct. 21, 2013  (AU) .............................. 2013904049
Aug. 29, 2014  (NZ) ....................................... 629531

(51) Int. Cl.
*A61M 16/16*    (2006.01)
*A61M 16/00*    (2006.01)
(Continued)

(52) U.S. Cl.
CPC ........ *A61M 16/16* (2013.01); *A61M 16/0051* (2013.01); *A61M 16/0066* (2013.01);
(Continued)

(58) Field of Classification Search
CPC .. A61M 16/16; A61M 16/109; A61M 16/006; A61M 16/06; A61M 2205/3334;
(Continued)

(56) References Cited

U.S. PATENT DOCUMENTS

| | | | | |
|---|---|---|---|---|
| 4,729,236 A | * | 3/1988 | Samborsky | ........... G01M 3/007 73/1.25 |
| 4,944,310 A | | 7/1990 | Sullivan | |

(Continued)

FOREIGN PATENT DOCUMENTS

| | | |
|---|---|---|
| WO | 2006015416 A1 | 2/2006 |
| WO | 2008148154 A1 | 12/2008 |

(Continued)

OTHER PUBLICATIONS

First Examination Report issued in corresponding NZ application No. 749883 on Jan. 25, 2019.
(Continued)

*Primary Examiner* — Timothy A Stanis
(74) *Attorney, Agent, or Firm* — Botos Churchill IP Law LLP

(57) ABSTRACT

Methods of an apparatus determine a quantity of a body of water in a humidifier such as by indirect measurement. The quantity of water may be determined by measuring one or more properties or characteristics, from which the quantity of water may be inferred. Characteristics of a flow of air, the humidifier, and/or the body of water may be measured. The characteristics may be, for example, pressure, flow rate, noise, vibration, temperature, electrical or mechanical. These may be measured by one or more sensors, which may be located in the humidifier, RPT device, air circuit or the patient interface. The methods described may have advantages, for example in being able to detect the quantity of water without requiring sensors to be present in a disposable (Continued)

component, and in some cases, without introduction of additional sensors.

20 Claims, 27 Drawing Sheets

(51) Int. Cl.
*A61M 16/06* (2006.01)
*A61M 16/10* (2006.01)

(52) U.S. Cl.
CPC ...... *A61M 16/026* (2017.08); *A61M 16/0633* (2014.02); *A61M 16/109* (2014.02); *A61M 2016/0027* (2013.01); *A61M 2016/003* (2013.01); *A61M 16/06* (2013.01); *A61M 16/1055* (2013.01); *A61M 16/107* (2014.02); *A61M 2205/3334* (2013.01); *A61M 2205/3368* (2013.01); *A61M 2205/3375* (2013.01); *A61M 2205/3389* (2013.01); *A61M 2205/50* (2013.01); *A61M 2205/70* (2013.01); *A61M 2210/0618* (2013.01)

(58) Field of Classification Search
CPC ....... A61M 2205/3389; F24F 2006/008; F24F 11/0008
See application file for complete search history.

(56) References Cited

U.S. PATENT DOCUMENTS

| | | | | |
|---|---|---|---|---|
| 5,636,548 | A | * | 6/1997 | Dunn ...................... G01F 23/72 |
| | | | | 73/1.73 |
| 5,797,057 | A | * | 8/1998 | Kinoshita ............... G03D 3/065 |
| | | | | 396/641 |
| 5,950,487 | A | * | 9/1999 | Maresca, Jr. ......... G01F 23/686 |
| | | | | 250/577 |
| 6,078,729 | A | | 6/2000 | Kopel |
| 6,220,091 | B1 | | 4/2001 | Chen |
| 6,237,593 | B1 | | 5/2001 | Brydon |
| 6,532,959 | B1 | | 3/2003 | Berthon-Jones |
| 7,866,944 | B2 | | 1/2011 | Barton et al. |
| 8,636,479 | B2 | | 1/2014 | Barton et al. |
| 8,638,014 | B2 | | 1/2014 | David |
| 2002/0189345 | A1 | | 12/2002 | Mulvaney |
| 2005/0203469 | A1 | * | 9/2005 | Bobroff .................. A61M 1/73 |
| | | | | 604/318 |
| 2006/0029179 | A1 | | 2/2006 | Srinivasan |
| 2006/0288777 | A1 | * | 12/2006 | Lazaris ............... A47J 31/4457 |
| | | | | 73/313 |
| 2009/0090363 | A1 | * | 4/2009 | Niland ................ A61M 16/122 |
| | | | | 128/203.26 |
| 2009/0158934 | A1 | * | 6/2009 | Jang ...................... F24F 13/222 |
| | | | | 96/189 |
| 2009/0184832 | A1 | | 7/2009 | Lloyd et al. |
| 2011/0023874 | A1 | | 2/2011 | Bath et al. |
| 2012/0168973 | A1 | | 7/2012 | Choi |
| 2013/0081625 | A1 | * | 4/2013 | Rustad ................ A61M 16/109 |
| | | | | 219/553 |
| 2013/0081701 | A1 | | 4/2013 | Korneff et al. |
| 2013/0104886 | A1 | | 5/2013 | Barker et al. |
| 2013/0174841 | A1 | | 7/2013 | Mcauley et al. |
| 2014/0238940 | A1 | * | 8/2014 | Schwarz ............. B01D 63/087 |
| | | | | 210/257.2 |
| 2015/0306335 | A1 | * | 10/2015 | Winski .................. A61M 16/16 |
| | | | | 128/203.14 |

FOREIGN PATENT DOCUMENTS

| | | |
|---|---|---|
| WO | 2012171072 A1 | 12/2012 |
| WO | 2013020167 A1 | 2/2013 |
| WO | 2013080107 A1 | 6/2013 |
| WO | 2014000039 A1 | 1/2014 |
| WO | 2015058255 A1 | 4/2015 |

OTHER PUBLICATIONS

Wikipedia, Level sensor [retrieved from internet on Nov. 12, 2014] <URL: http://web.archive.org/web/*/http://en.wikipedia.org/wiki/Level_sensor> published on Nov. 13, 2007 as per Wayback Machine.
Wikipedia, Pressure sensor [retrieved from internet on Nov. 12, 2014] <URL: http:/web.archive.org/web/*/http://en.Wikipedia.org/wiki/Pressure_sensor > published on Nov. 17, 2007 as perWayback Machine.
Examination Report issued in corresponding EP application No. 784221 on Feb. 8, 2022.
International Search Report and Written Opinion for Application No. PCT/AU2014/050286 dated Dec. 18, 2014.
West, John B, "Respiratory Physiology", Lippincott Williams & Wilkins, 9th edition published 2011, 211 pp.

* cited by examiner

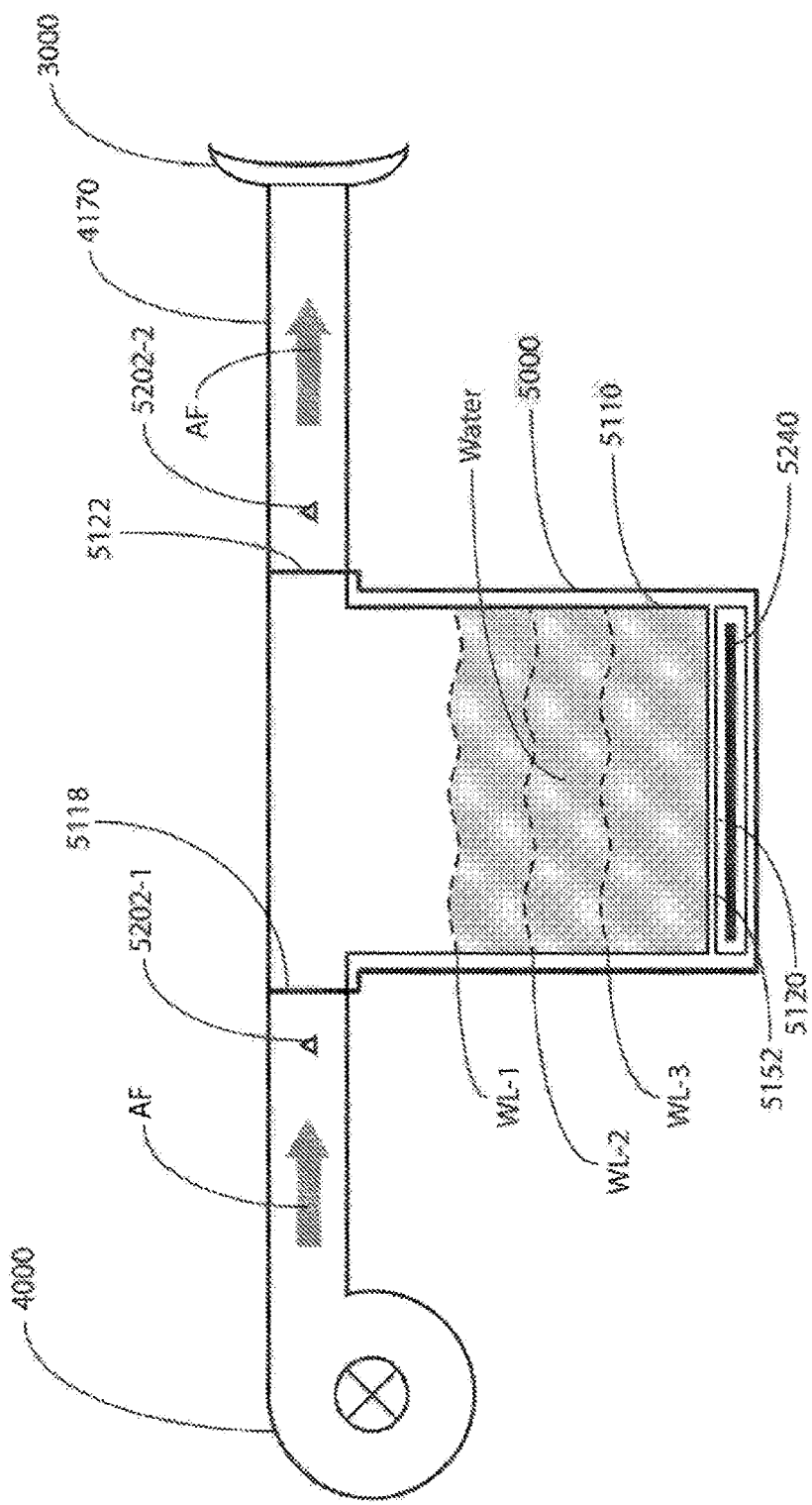

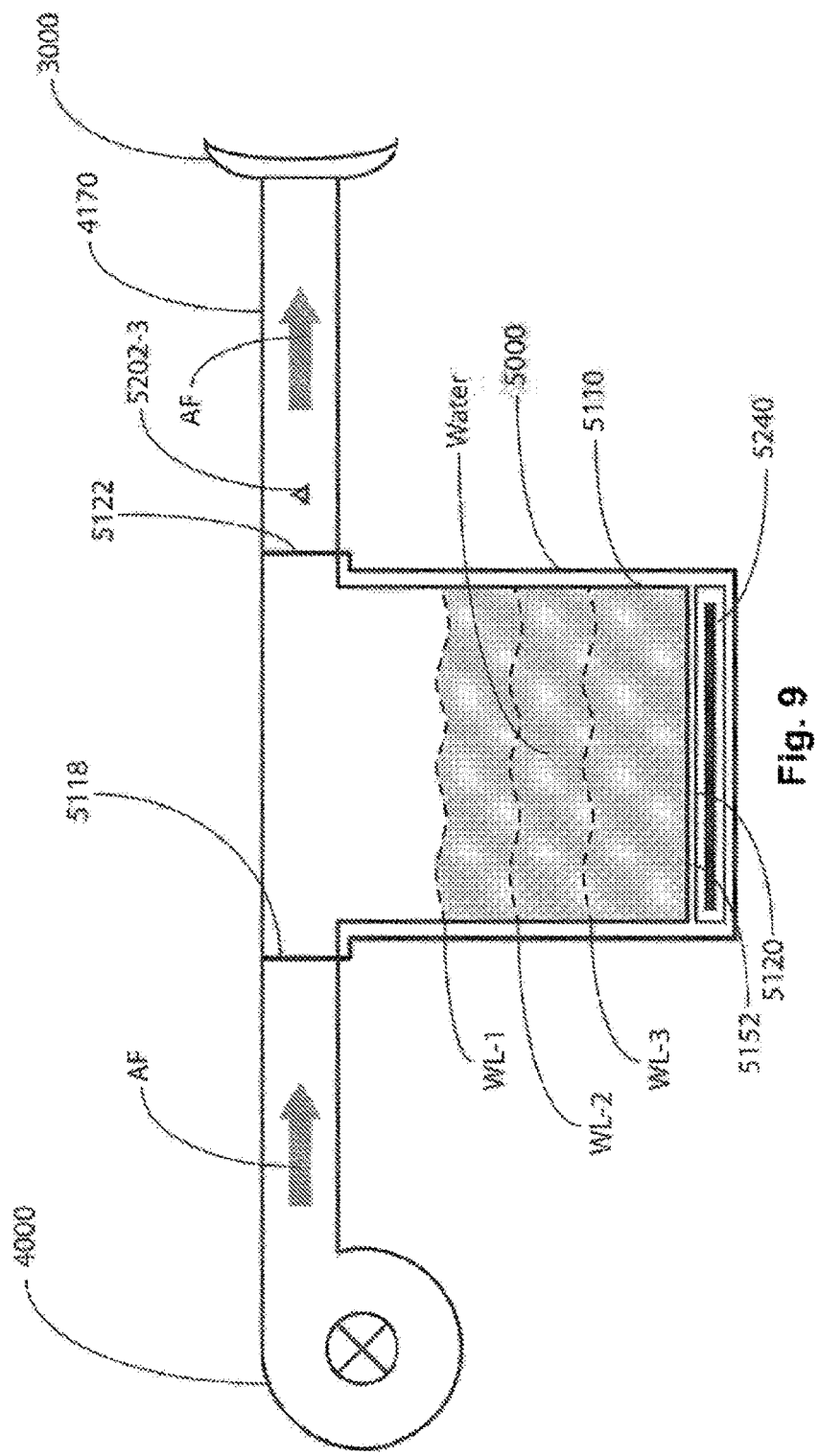

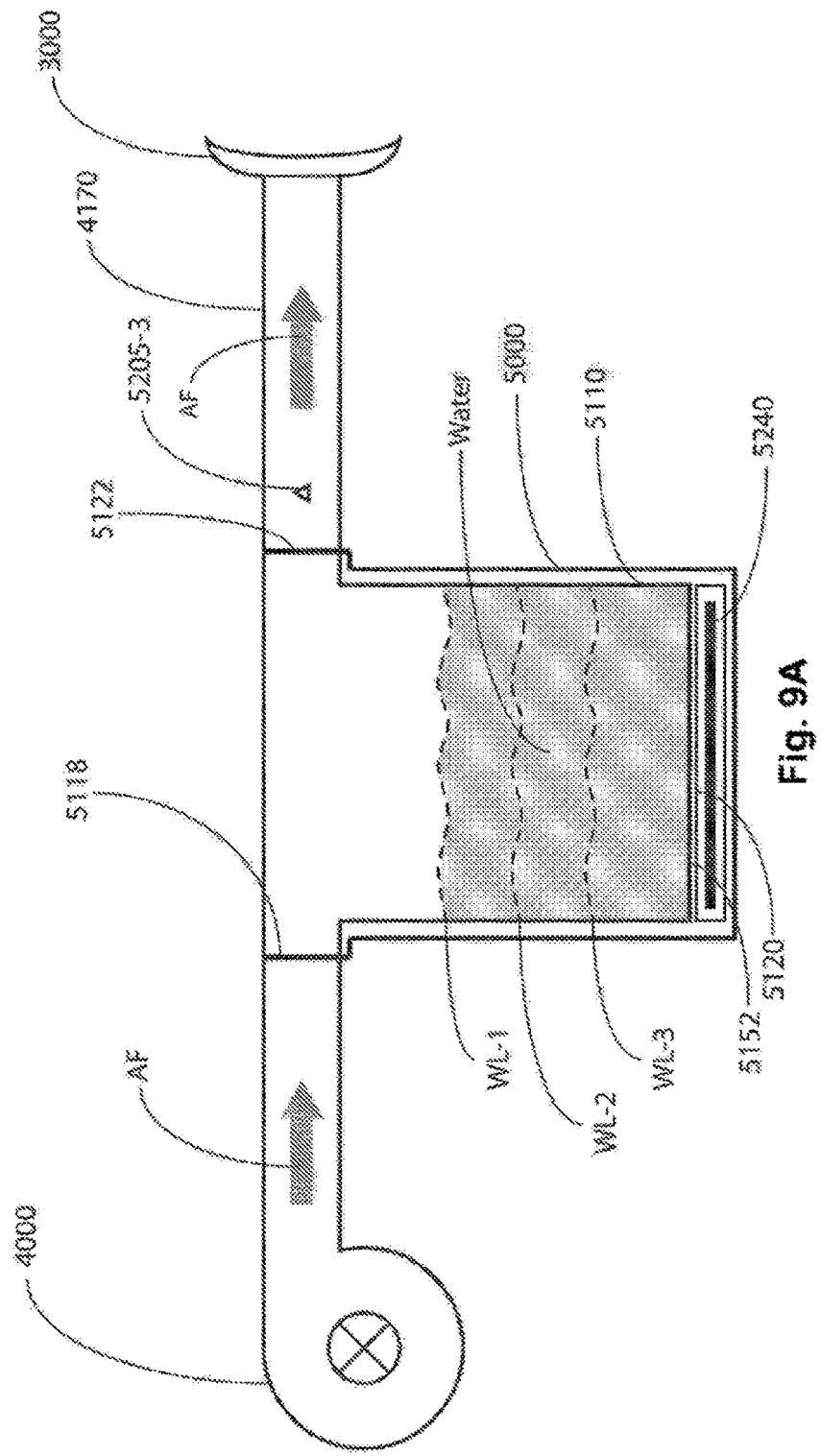

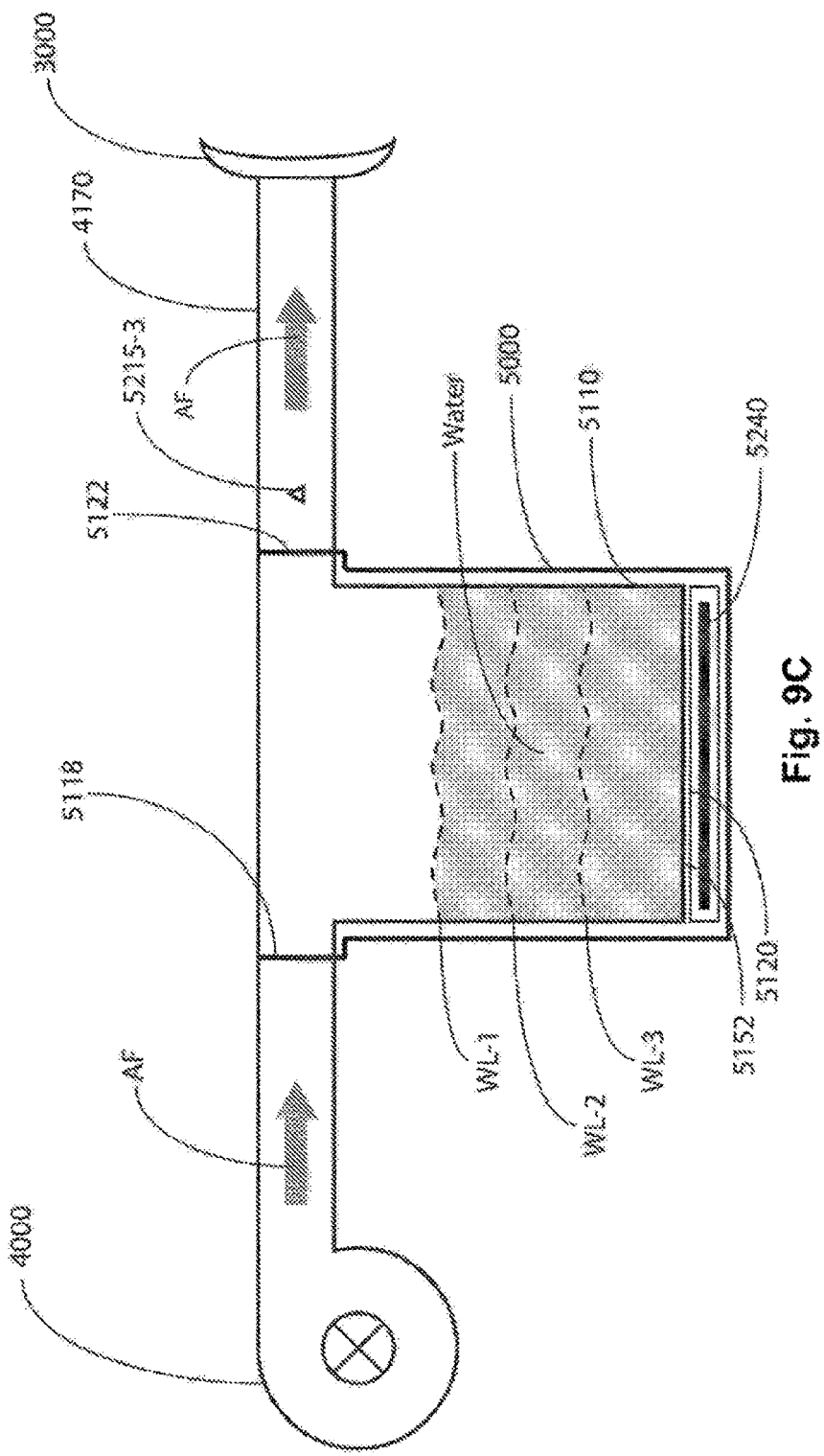

METHODS OF DETECTING A QUANTITY OF WATER IN A HUMIDIFIER

1 CROSS-REFERENCE TO RELATED APPLICATIONS

This application is a continuation of U.S. patent application Ser. No. 15/030,402 filed Apr. 19, 2016 which is a national phase entry under 35 U.S.C. § 371 of International Application No. PCT/AU2014/050286 filed Oct. 14, 2014, published in English, which claims priority from New Zealand Patent Application No. 629531 filed Aug. 29, 2014 and Australian Provisional Patent Application No. 2013904049 filed Oct. 21, 2013, all of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2011.

A range of respiratory disorders exist. Certain disorders may be characterised by particular events, e.g., apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients, CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g., Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g., Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Diagnosis and Treatment Systems

These therapies may be provided by a treatment system or device. Systems and devices may also be used to diagnose a condition without treating it.

A treatment system may comprise a Respiratory Pressure Therapy Device (RPT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable, especially when worn for long periods of time or when a patient is unfamiliar with a system. For example, masks designed solely for aviators, masks designed as part of personal protection equipment (e.g., filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g., aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

Air pressure generators are known in a range of applications, e.g., industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO3744 in CPAP mode at 10 $cmH_2O$).

| RPT Device name | A-weighted sound power level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i ™ Humidifier | 28.6 | 2010 |

One known RPT device used for treating sleep-disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

2.2.4 Humidifier

Delivery of a flow of air without humidification may cause drying of airways. The use of a humidifier with a RPT device and the patient interface produces humidified gas that minimizes drying of the nasal mucosa and increases patient airway comfort. In addition, in cooler climates, warm air applied generally to the face area in and about the patient interface is more comfortable than cold air. A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g., at a hospital). A medical humidifier for bedside placement may be small. A medical humidifier may be configured to only humidify and/or heat the flow of air delivered to the patient without humidifying and/or heating the patient's surroundings. Room-based systems (e.g., a sauna, an air conditioner, or an evaporative cooler), for example, may also humidify air that is breathed in by the patient; however, those systems would also humidify and/or heat the entire room, which may cause discomfort to the occupants. Furthermore, medical humidifiers may have more stringent safety constraints than industrial humidifiers.

While a number of medical humidifiers are known, they can suffer from one or more shortcomings. Some medical humidifiers may provide inadequate humidification, and some are difficult or inconvenient to use by patients.

Humidity refers to the quantity of water vapour present in the air. It is commonly measured in two ways:

(1) Absolute Humidity (AH) is the actual content of water vapour in the air recorded in terms of weight per volume—usually in grams per cubic meter (g/m3) or milligrams per liter (mg/L).
(2) Relative Humidity (RH) is a percentage expression of the actual water vapour content of a gas compared to its capacity to carry water vapour at any given temperature.

The capacity of air to hold water vapour increases as the temperature of the air increases. This means that for air with a stable AH, the RH will decline as the temperature of the air is increased. Conversely, for air saturated with water (100% RH), if the temperature is reduced then the excess water will condense out. Air breathed by humans is generally naturally heated and humidified by the patient's airways to reach a temperature of 37° C. and 100% humidity. At this temperature, the absolute humidity (AH) is 44 mg/L.

Medical humidifiers are available in many forms. A medical humidifier may be a standalone device that is coupled to an RPT device via an air circuit, integrated with the RPT device or configured to be directly coupled to the relevant RPT device. While passive humidifiers can provide some relief, generally, a heated humidifier is required to provide sufficient humidity and temperature to the air so that the patient will be comfortable. Humidifiers typically comprise a humidifier reservoir (also referred to as water reservoir or tub) having a capacity of several hundred milliliters (ml), a heating element for heating the water in the reservoir, a control to enable the level of humidification to be varied, a gas inlet to receive gas from the flow generator or device, and a gas outlet adapted to be connected to an air circuit that delivers the humidified gas to the patient interface.

A heated passover humidifier is one common form of humidifier used with a RPT device. In such humidifiers, the heating element may be incorporated in a heating plate which sits under, and is in thermal contact with, the humidifier reservoir. Thus, heat is transferred from the heating plate to the humidifier reservoir primarily by conduction. The air flow from the RPT device or flow generator or ventilator passes over the heated water in the water tub, resulting in water vapour being taken up by the air flow. The ResMed H4i™ and H5i™ Humidifiers are examples of such heated passover humidifiers that are used in combination with ResMed S8 and S9 CPAP systems respectively.

Other humidifiers may also be used, such as a bubble or diffuser humidifier, a jet humidifier or a wicking humidifier.

An alternative form of humidification is provided by the ResMed HumiCare™ D900 humidifier that uses a Counter-Stream™ technology that directs the air flow over a large surface area in a first direction, whilst supplying heated water to the large surface area in a second opposite direction. The ResMed HumiCare™ D900 humidifier may be used with a range of invasive and non-invasive ventilators.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

One form of the present technology relates to a method of determining a quantity of a body of liquid in a humidifier.

Some versions of the present technology may involve a method of determining a reservoir water quantity of a humidifier. The method may include providing a humidifier reservoir configured to contain water, the reservoir being in fluid communication with an inlet of the humidifier. The method may further include delivering a flow of air to the humidifier reservoir through the inlet of the humidifier. The method may further include determining a first measurement set from the flow of air. The method may further include determining a reservoir water quantity of the humidifier reservoir based on the first measurement set.

In some versions, the first measurement set may comprise one or more sensed values of any one or more of: a pressure, a temperature, a flow rate and a noise. In some versions, a sensed value of the first measurement set may be determined with a first sensor at a location downstream of an outlet of the humidifier reservoir. In some versions, the location of the first sensor may be external to the humidifier reservoir. In some versions, a sensed value of the first measurement set may be determined with a first sensor located outside of the humidifier reservoir. In some versions, the reservoir water quantity may be determined with the first measurement set and reference data. In some versions, the reference data may comprise a second measurement set including one or more sensed values.

In some versions, the second measurement set may comprise one or more sensed values of one or more of: a pressure, a temperature, a flow rate and a noise. In some versions, the second measure set may be determined subsequent to determination of the first measure set. In some versions, the second measure set may be determined at least a predetermined length of time subsequent to determination of the first measure set. In some versions, the reference data may comprise one or more estimates of one or more of: a pressure, a temperature, a flow rate and a noise. In some versions, the one or more estimates may be based on one or more of: a motor current, a motor speed, a motor acceleration, an altitude, a therapy pressure and a flow rate. In some versions, determining the reservoir water quantity may be based on a function of the reference data and the first measurement set.

In some versions, the function may determine a change in magnitude of one or more values of the reference data and the first measurement set. In some versions, the function may determine a change in phase of one or more values of the reference data and the first measurement set. In some versions, the function may determine a time lag with one or more values of the reference data and the first measurement set. In some versions, the reference data may comprise one or more sensed values determined with a second sensor at a location different from the first sensor. In some versions, the second sensor may be located upstream of the humidifier reservoir. In some versions, the reservoir water quantity may be determined by locating a value in a look-up table with a value of the first measurement set.

In some versions, the method may include performing a calibration cycle to populate one or more values in the look-up table. In some versions, the reservoir water quantity may be determined with a function. In some versions, the method may include performing a calibration cycle to determine the function. In some versions, the calibration cycle may be performed while the humidifier reservoir is in use. In some versions, the calibration cycle may be performed during a set-up process. In some versions, the calibration cycle may be repeated at predetermined time intervals.

Some versions of the present technology may involve a control method of a processor for indirectly determining a reservoir water quantity of a humidifier having a reservoir to contain water, the humidifier having an inlet and an outlet. The method may include, in the processor, determining with a first sensor a first property, the first property comprising one of a characteristic of the humidifier, a characteristic of a flow of air through the humidifier, and a characteristic of the water in the humidifier reservoir. The method may further include, in the processor, determining the reservoir water quantity based on the first property.

In some versions, the first property may comprise a capacitance or resistance of the water. In some versions, first property may comprise a frequency of a vibration in the humidifier reservoir. In some versions, the first property may comprise a pressure drop through the inlet of the humidifier and the outlet of the humidifier. In some versions, the first property may comprise a time lag through the inlet and the outlet of the humidifier. In some versions, the first property may comprise a torque of a rotatable paddle in the humidifier. In some versions, the first property may comprise a noise in the humidifier.

In some versions, the first property may comprise density of air through the humidifier. In some versions, the method may include determining a change with respect to first and second measurements of the first property, wherein the reservoir water quantity is determined from the determined change. In some versions, the method may include accessing a table of reservoir water quantity values in correlation with a value attributable to the first property. In some versions, the method may include controlling an adjustment of an operation of a respiratory treatment apparatus based on the determined reservoir water quantity. In some versions, the adjustment may comprise a change to a rate of humidification.

Some versions of the present technology may involve an apparatus for humidifying a flow of air to be delivered to a patient. The apparatus may include an inlet to receive the flow of air. The apparatus may further include a humidifier reservoir configured to contain a body of water for humidifying the flow of air, the humidifier reservoir being in fluid communication with the inlet. The apparatus may further include a first sensor configured to determine a first measurement set from the flow of air. The apparatus may further include a controller, wherein the controller is configured to determine a reservoir water quantity of the humidifier reservoir based on the first measurement set.

In some versions, the first measurement may comprise one or more sensed values of one or more of: a pressure, a temperature, a flow rate and a noise. In some versions, the first sensor may be located to sense values downstream of the humidifier reservoir. In some versions, the first sensor may be located external to the humidifier reservoir. In some versions, the controller may be configured to determine a quantity of the body of water based on the first measurement set and reference data. In some versions, the reference data may comprise a second measurement set including one or more sensed values. In some versions, the second measurement set may comprise one or more sensed values of one or more of: a pressure, a temperature, a flow rate and a noise. In some versions, the reference data may comprise one or more estimates of one or more of: a pressure, a temperature, a flow rate and a noise.

In some versions, the one or more estimates may be based on one or more of: a motor current, a motor speed, a motor acceleration, an altitude, a therapy pressure and a flow rate. In some versions, the controller may be further configured to determine the quantity of the body of water based on a relationship between the reference data and the first measurement set. In some versions, the relationship may include one or more of a change in magnitude, a change in phase, or a time lag between one or more values of the reference data and the first measurement set. In some versions, the controller may be further configured to determine the reservoir water quantity by finding one or more values in a look-up table corresponding to the first measurement or by processing a function on one or more values of the first measurement set. In some versions, the controller may be further configured to perform a calibration cycle to populate the one or more values in the look-up table or to derive the function.

Some versions of the present technology may involve an apparatus for humidifying a flow of air to be delivered to a patient, the apparatus for indirectly determining a reservoir water quantity. The apparatus may include a humidifier reservoir configured to contain a body of water for humidifying a flow of air, the humidifier reservoir being in fluid communication with an inlet and an outlet for the flow of air. The apparatus may further include one or more sensors. The apparatus may further include a controller coupled with the one or more sensors, the controller being configured to determine with the one or more sensors a first property, the first property comprising one of a characteristic of the humidifier, a characteristic of a flow of air through the humidifier, and a characteristic of water in the humidifier reservoir, the controller being further configured to determine the reservoir water quantity based on the first property.

In some versions, the first property may comprise a capacitance or resistance of the water. In some versions, the first property may comprise a frequency of a vibration in the humidifier reservoir. In some versions, the first property may comprise a pressure drop through an inlet of the humidifier and the outlet of the humidifier. In some versions, the first property may comprise a time lag through the inlet and the outlet of the humidifier. In some versions, the first property may comprise a torque of a rotatable paddle in the humidifier. In some versions, the first property may comprise a noise in the humidifier. In some versions, the first property may comprise density of air through the humidifier.

In some versions, the controller may be further configured to determine a change with respect to first and second measurements of the first property, wherein the reservoir water quantity is determined from the determined change. In some versions, the controller may be further configured to access a table of reservoir water quantity values in correlation with a value attributable to the first property. In some versions, the controller may be further configured to make an adjustment of an operation of a respiratory treatment apparatus based on the determined reservoir water quantity. In some versions, the adjustment may comprise a change to a rate of humidification.

Of course, portions of the aspects may form sub-aspects of the present technology. Also, various ones of the sub-aspects and/or aspects may be combined in various manners and may also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000. A bed partner 1100 is also shown.

4.2 Respiratory System and Facial Anatomy

Figure 1A:
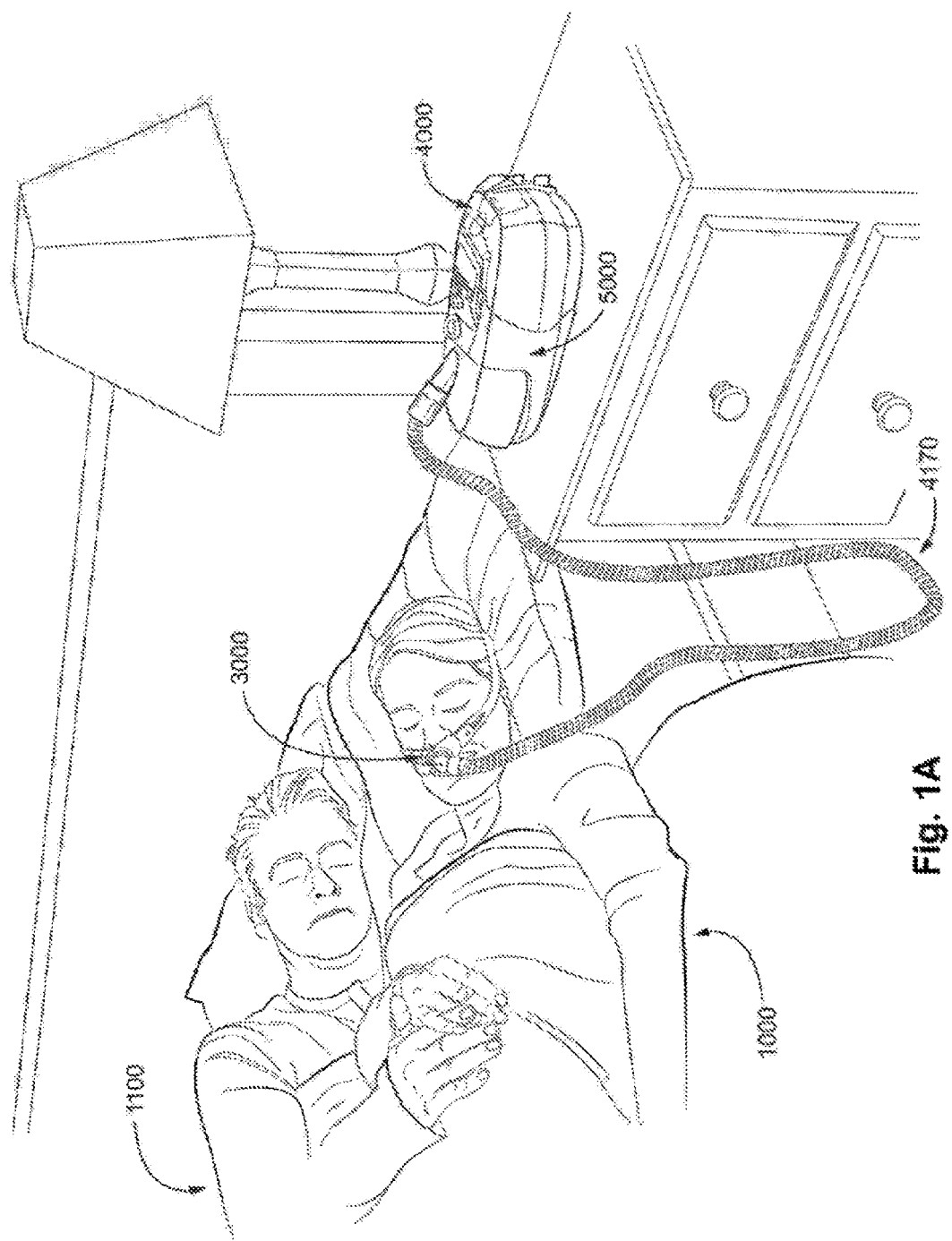
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 1B:
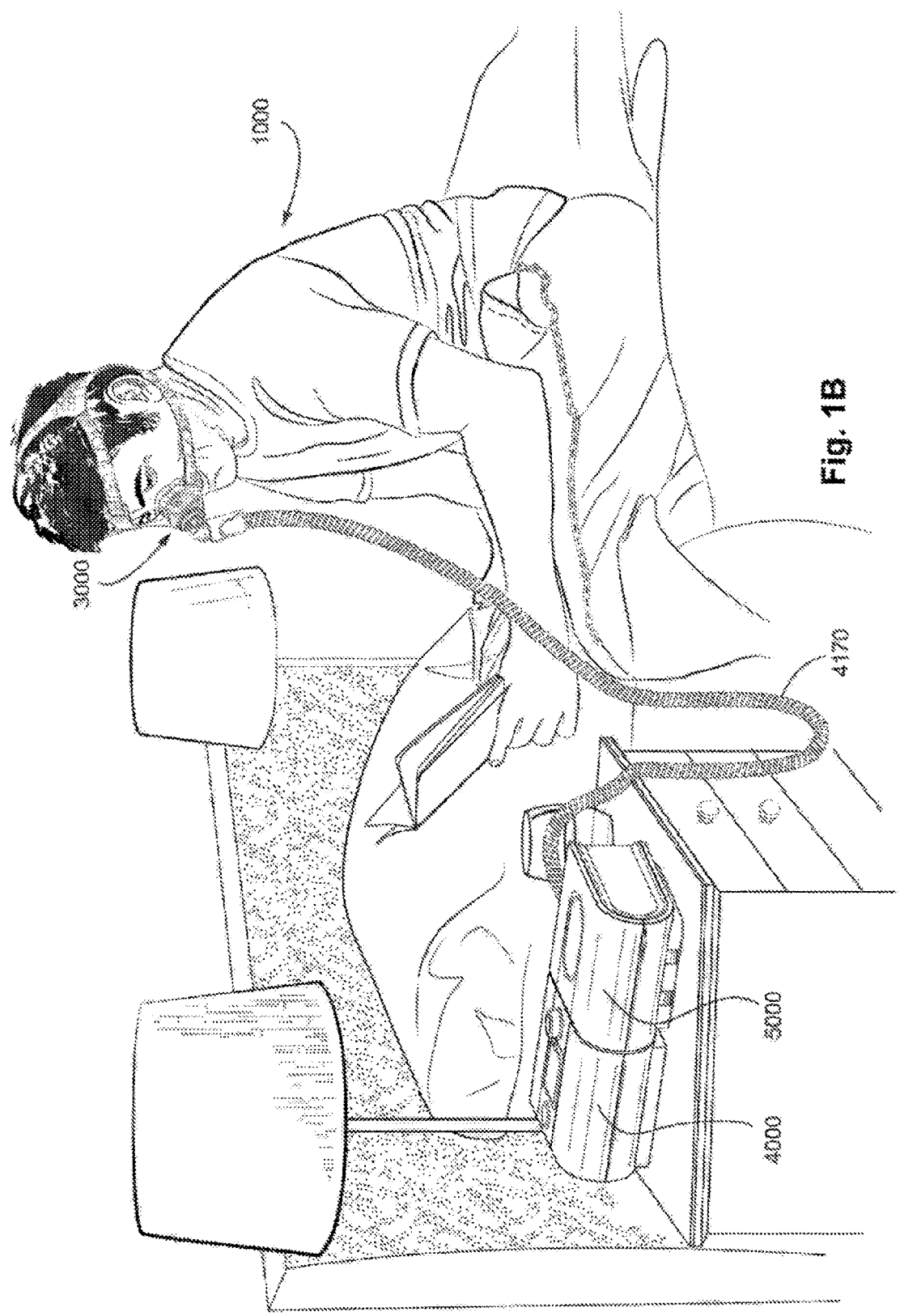
Figure 1C:
Figure 2A:
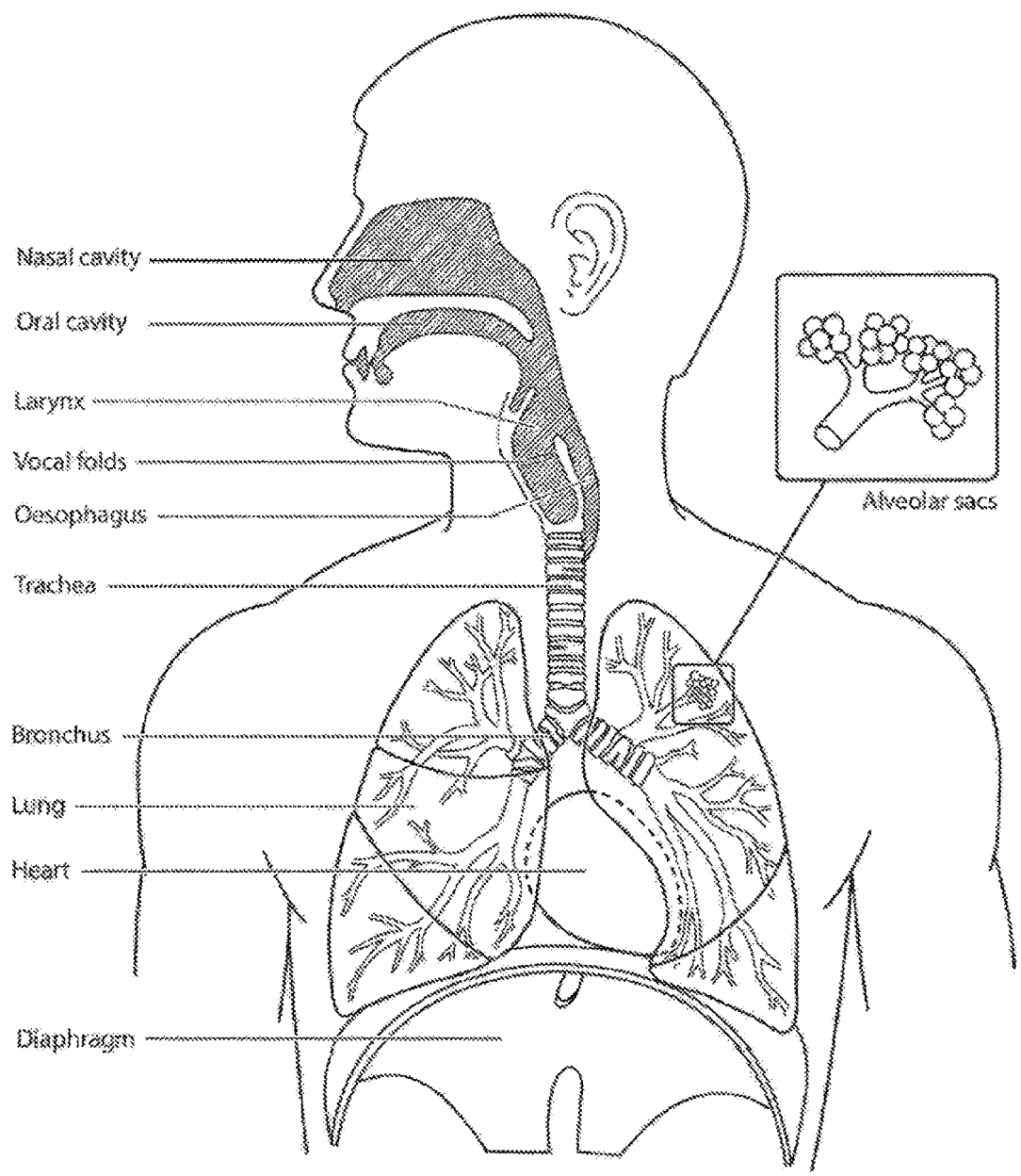

FIG. 2A shows an overview of a human respiratory system including the nasal and oral cavities, the larynx, vocal folds, esophagus, trachea, bronchus, lung, alveolar sacs, heart and diaphragm.

Figure 2B:
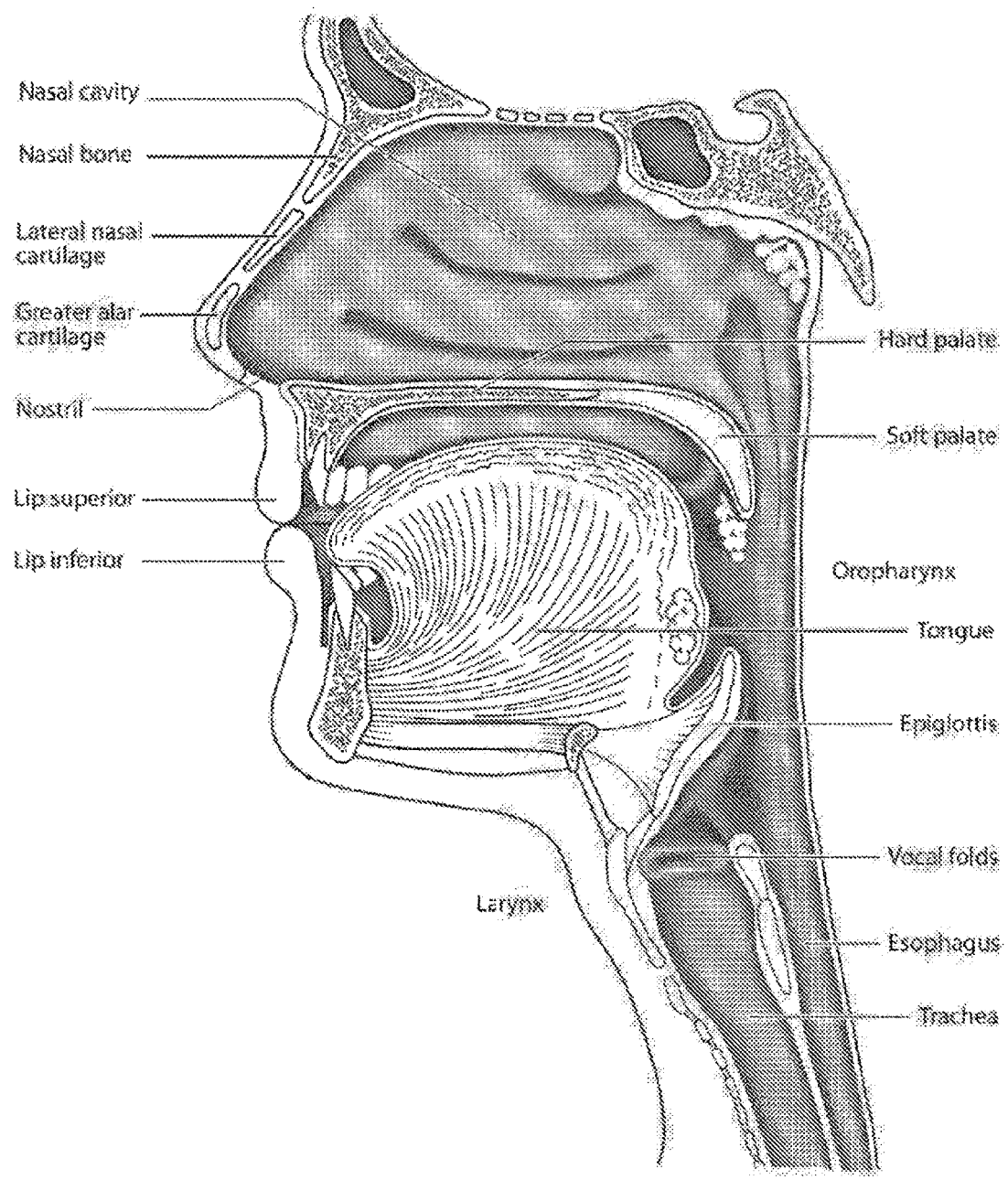

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, esophagus and trachea.

Figure 2C:
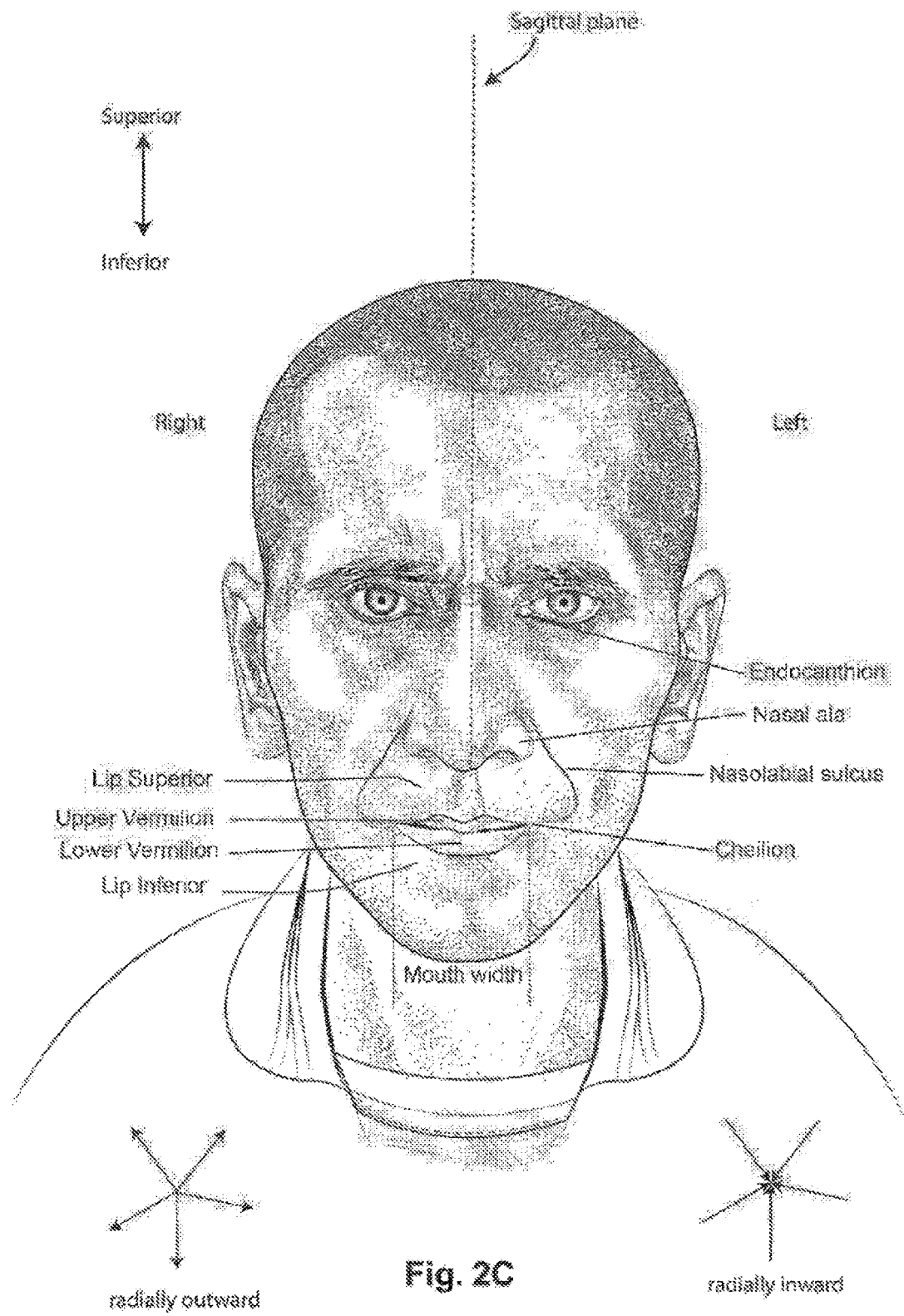

FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.

4.3 Patient Interface

Figure 3A:
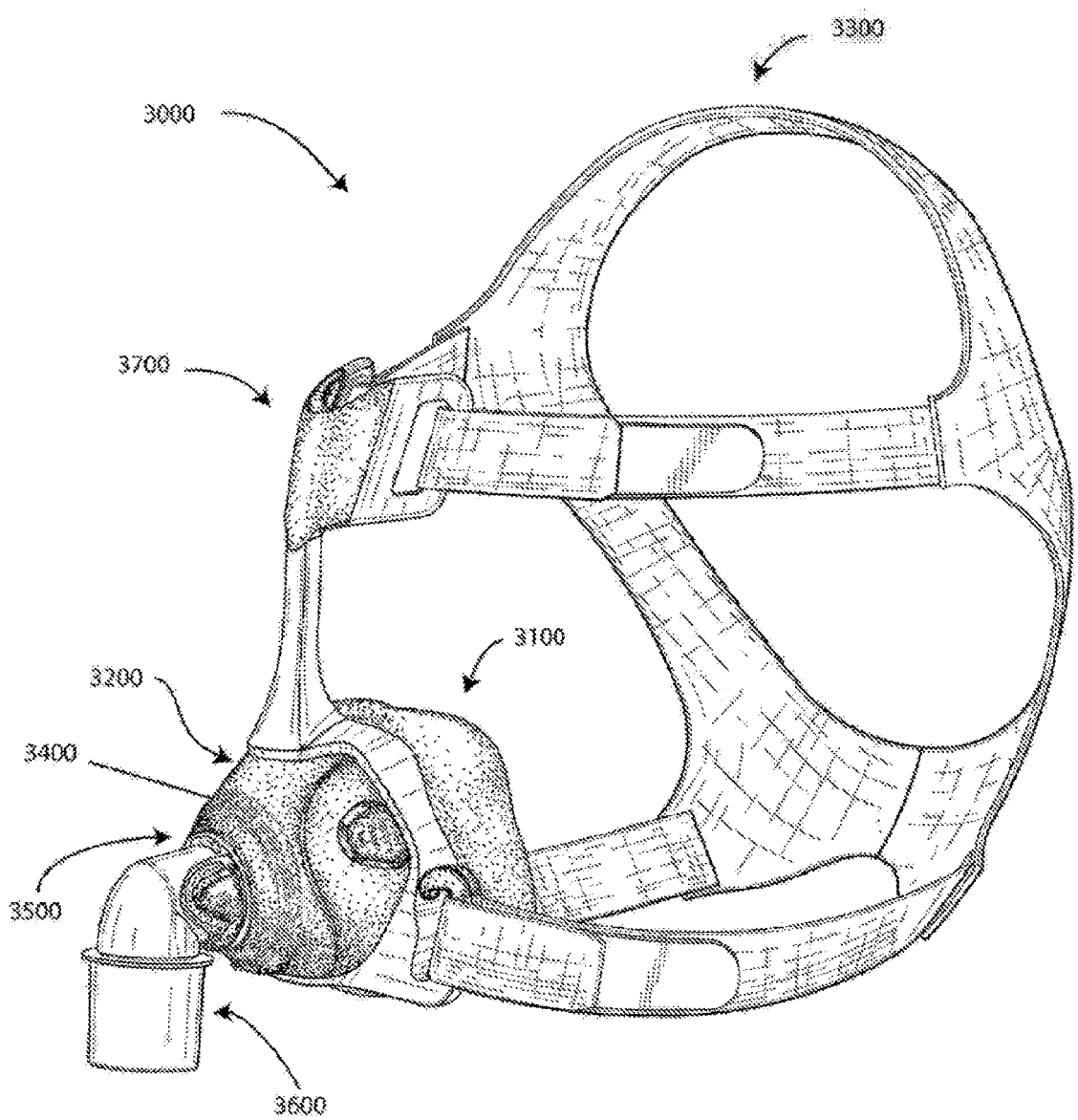

FIG. 3A shows a patient interface in the form of a nasal mask in accordance with one form of the present technology.

4.4 RPT Device

Figure 4A:
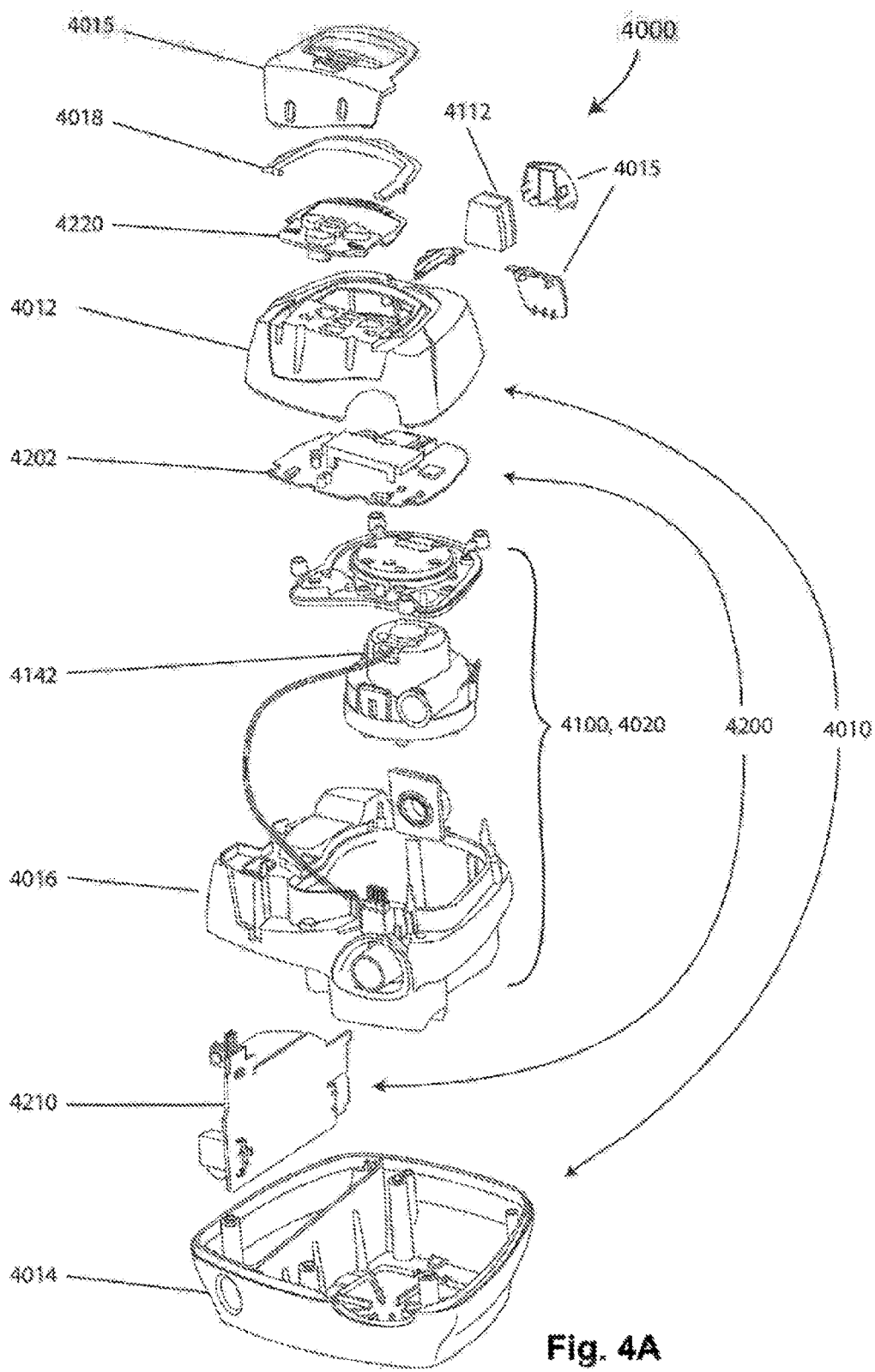

FIG. 4A shows an RPT device in accordance with one form of the present technology.

Figure 4B:
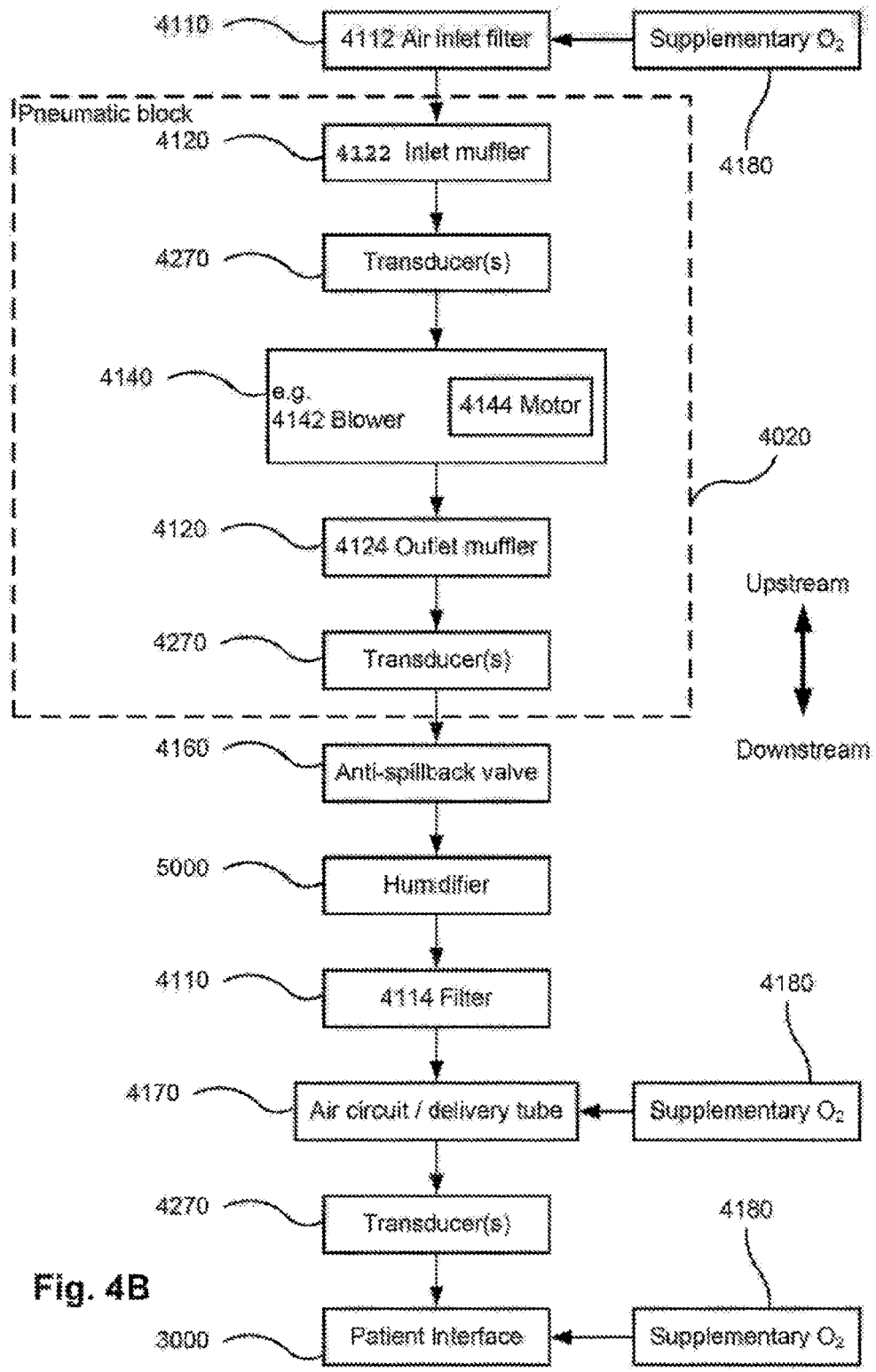

FIG. 4B is a schematic diagram of the pneumatic path of a RPT device in accordance with one form of the present technology. The directions of upstream and downstream are indicated.

Figure 4C:
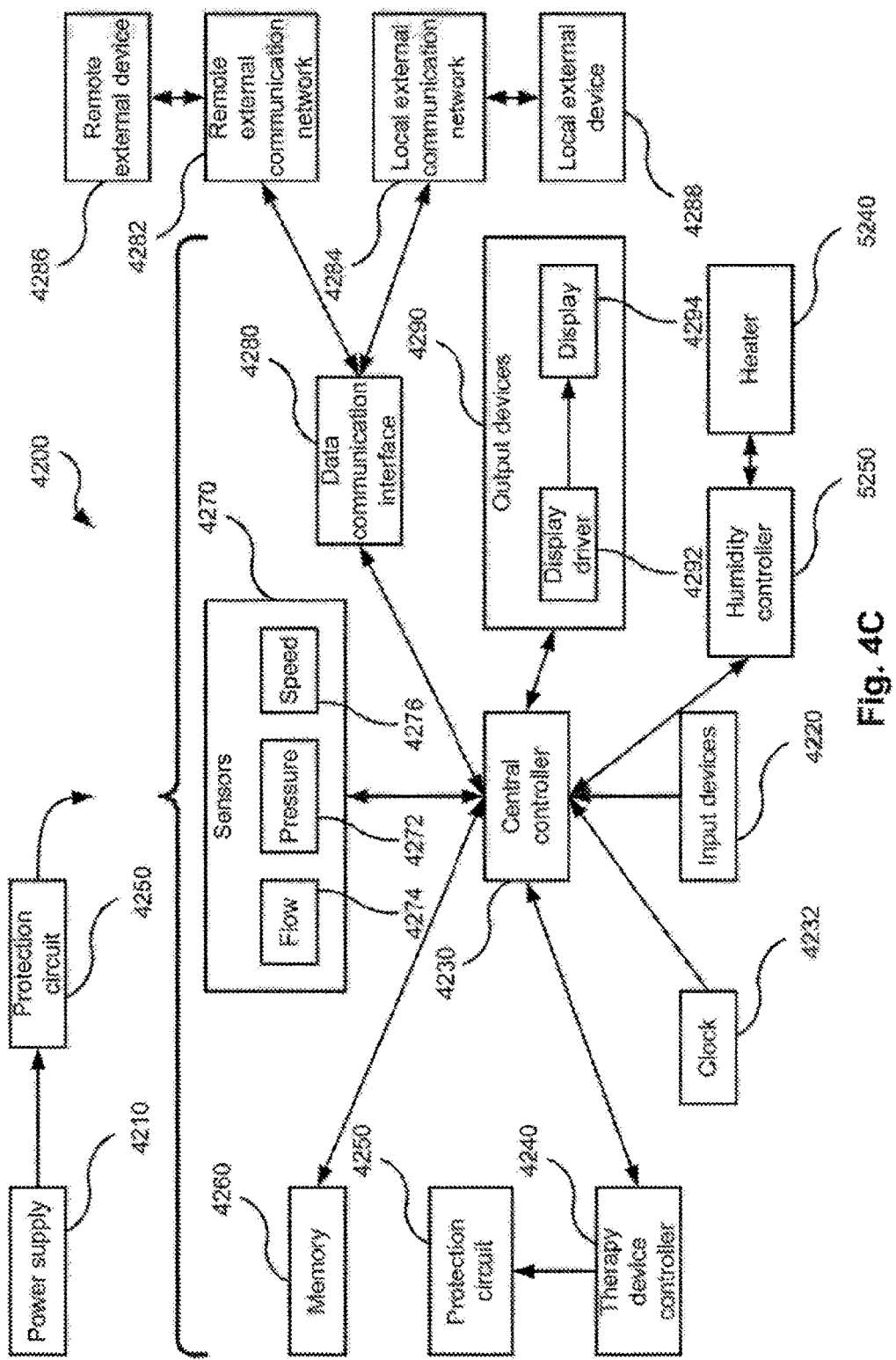

FIG. 4C is a schematic diagram of the electrical components of a RPT device in accordance with one form of the present technology.

4.5 Humidifier

Figure 5A:
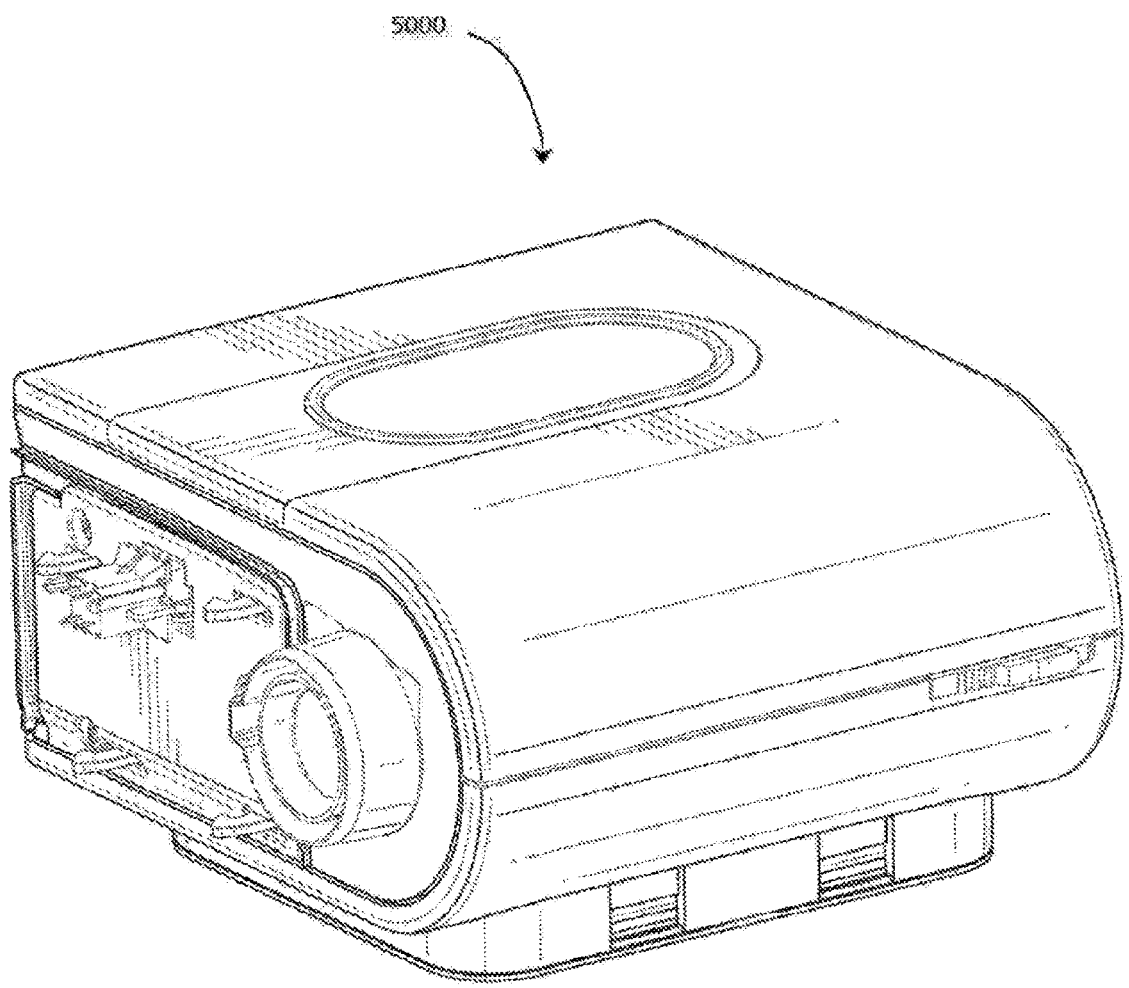

FIG. 5A shows an isometric view of a humidifier in accordance with one form of the present technology.

Figure 5B:
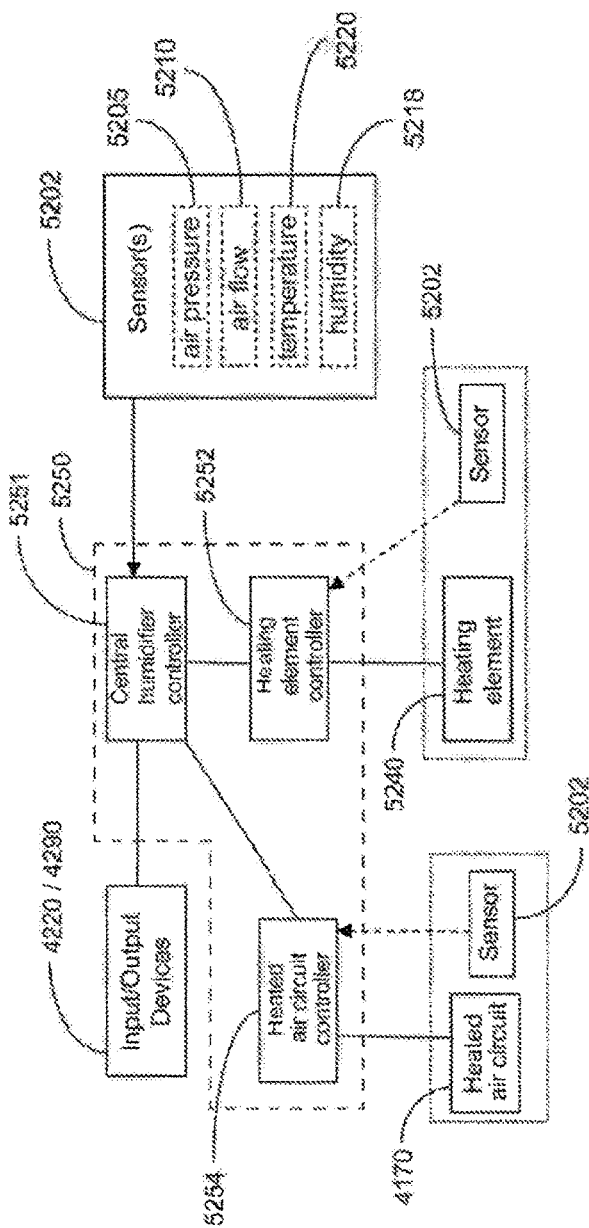

FIG. 5B shows a schematic of a humidifier in accordance with one form of the present technology.

Figure 5C:
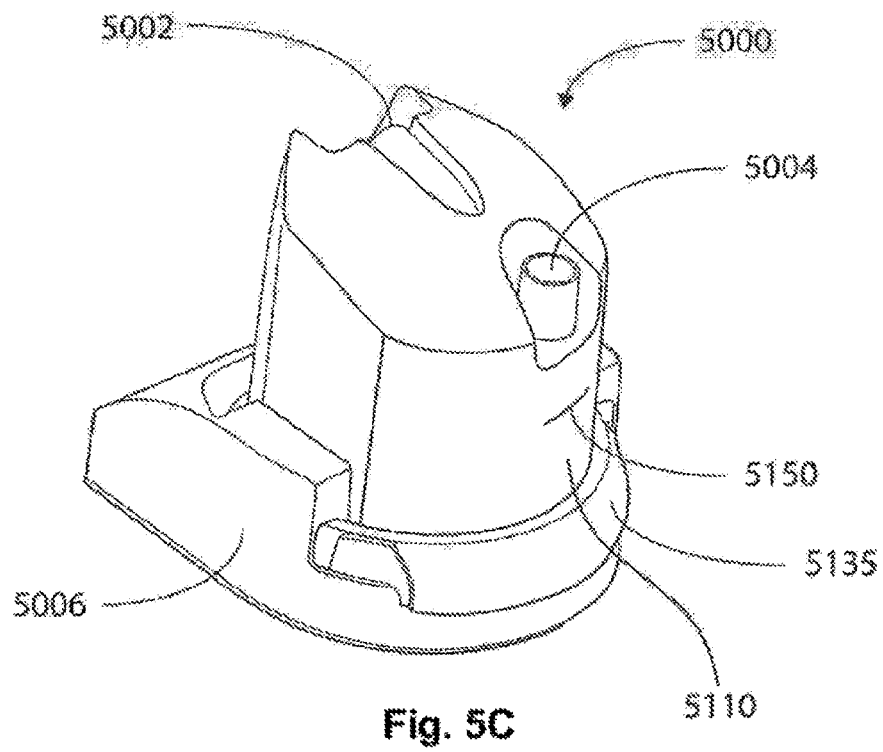

FIG. 5C shows an isometric view of a humidifier in accordance with one form of the present technology.

Figure 5D:
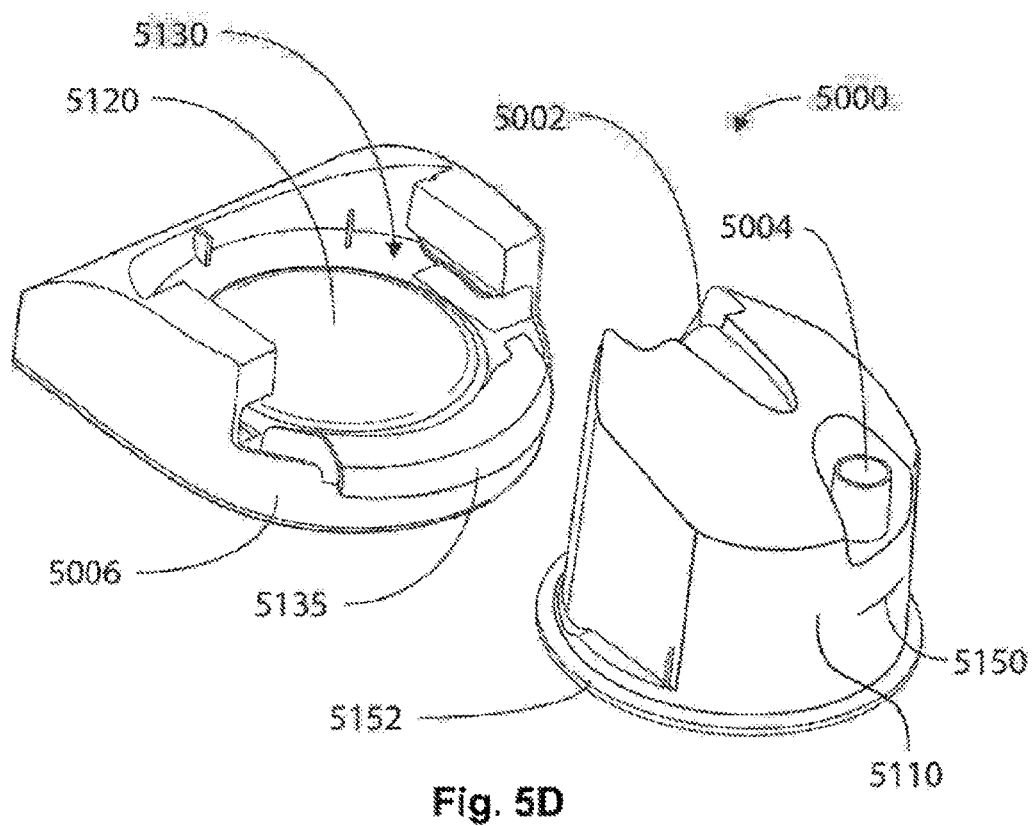

FIG. 5D shows an isometric view of a humidifier in accordance with one form of the present technology, showing a humidifier reservoir 5110 removed from the humidifier reservoir dock 5130.

FIG. 6 shows an exemplary schematic of a respiratory treatment system comprising a humidifier according to one aspect of the present technology, wherein the humidifier comprises a first sensor located upstream of the reservoir and a second sensor located downstream of the reservoir.

Figure 6A:
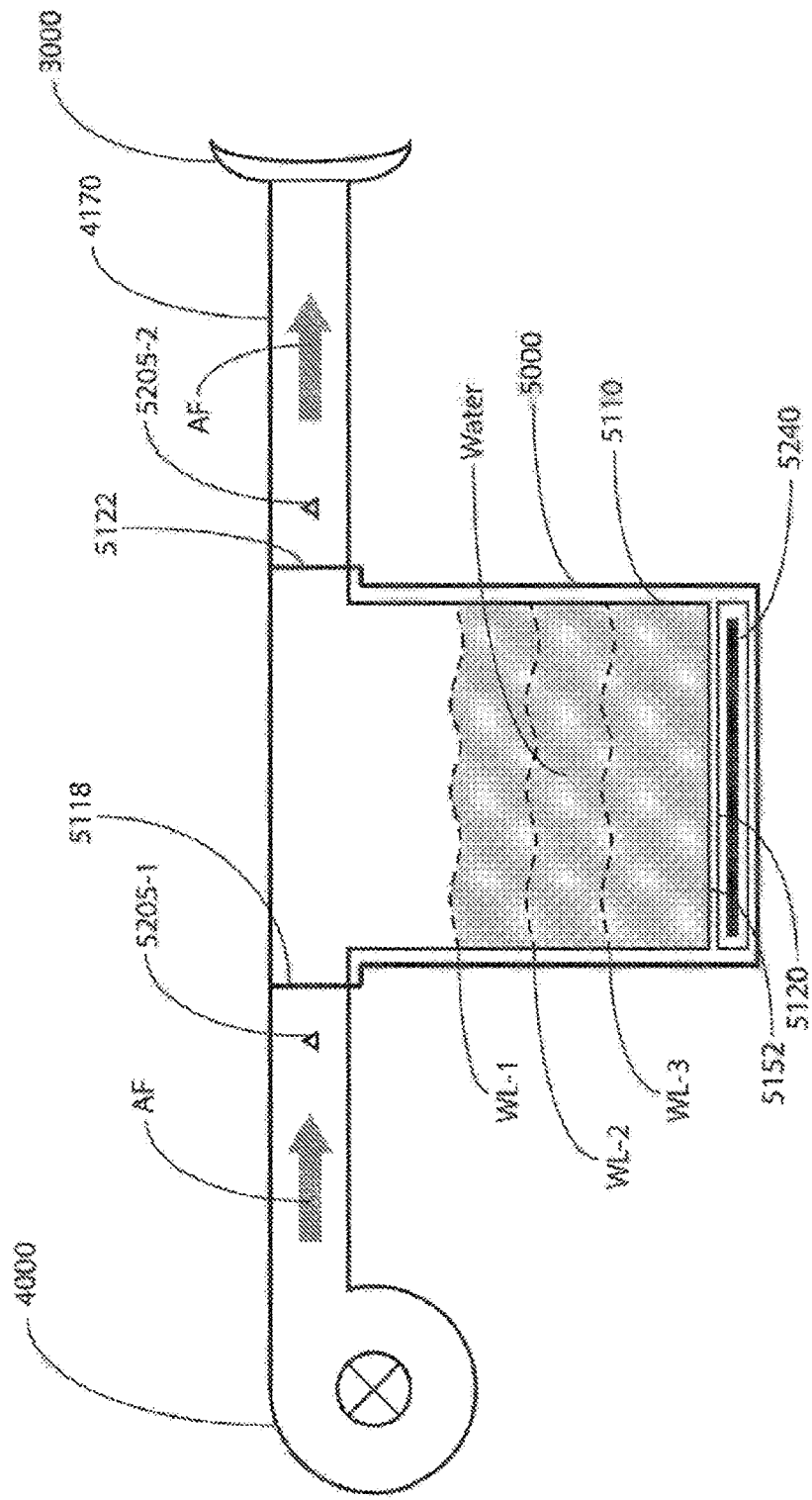

FIG. 6A shows an exemplary schematic of a respiratory treatment system comprising a humidifier according to one aspect of the present technology, wherein the humidifier comprises a first pressure sensor located upstream of the reservoir and a second pressure sensor located downstream of the reservoir.

Figure 6B:
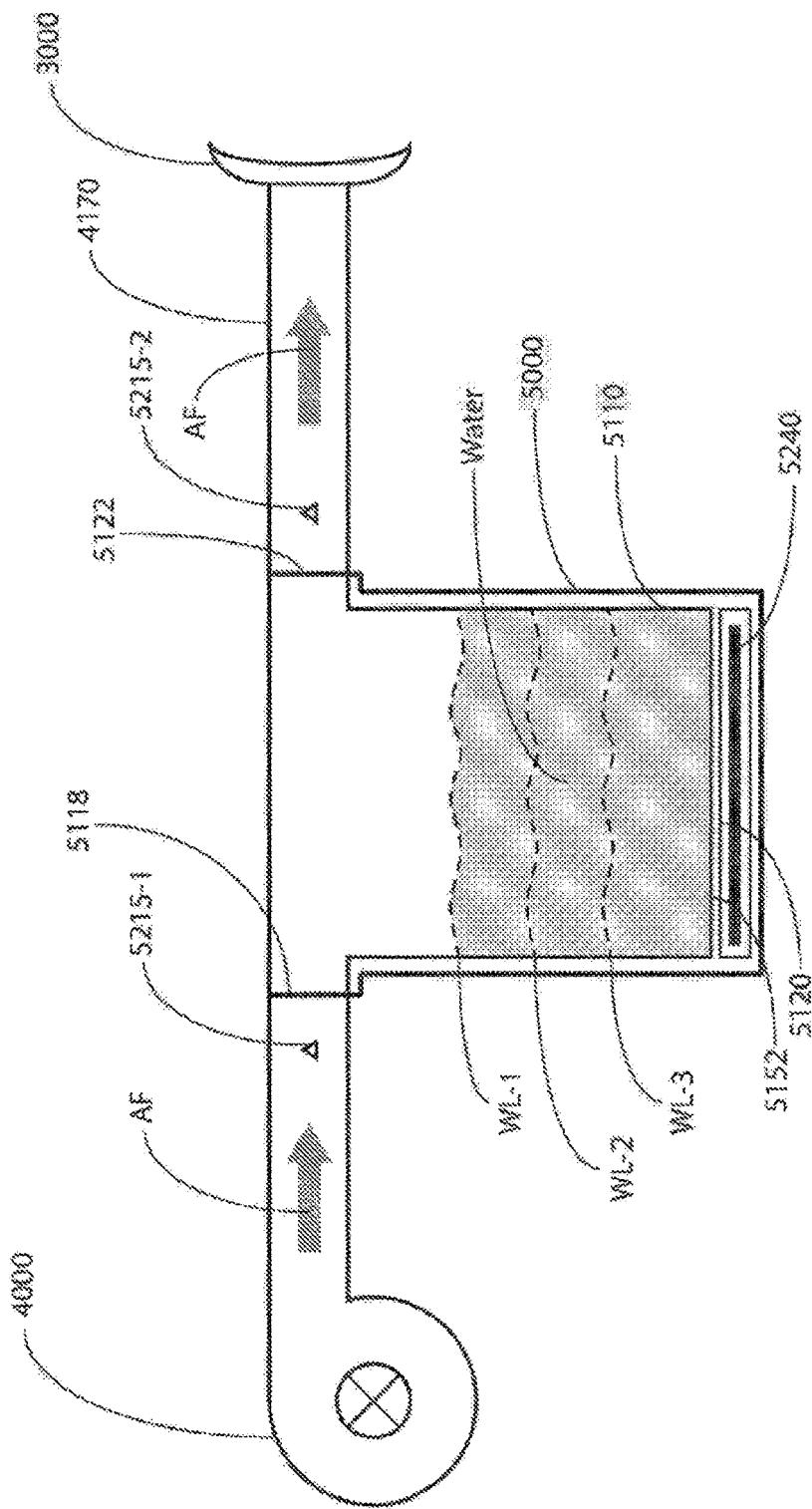

FIG. 6B shows an exemplary schematic of a respiratory treatment system comprising a humidifier according to one aspect of the present technology, wherein the humidifier comprises a first microphone located upstream of the reservoir and a second microphone located downstream of the reservoir.

Figure 6C:
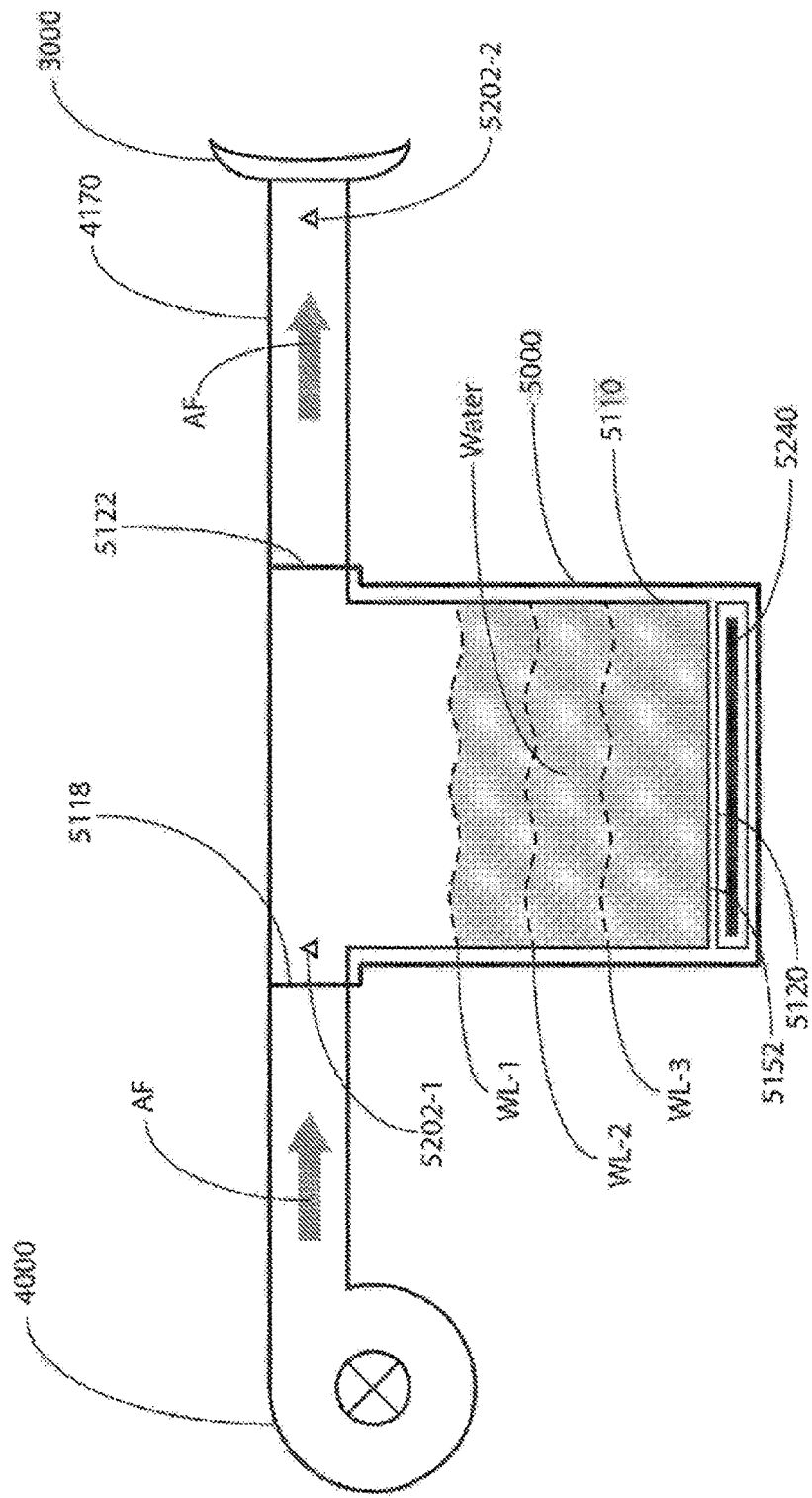

FIG. 6C shows an exemplary schematic of a respiratory treatment system comprising a humidifier according to one aspect of the present technology, wherein the humidifier comprises a first sensor located in the reservoir and a second sensor located downstream of the reservoir, proximal to a patient interface.

Figures 7, 8:
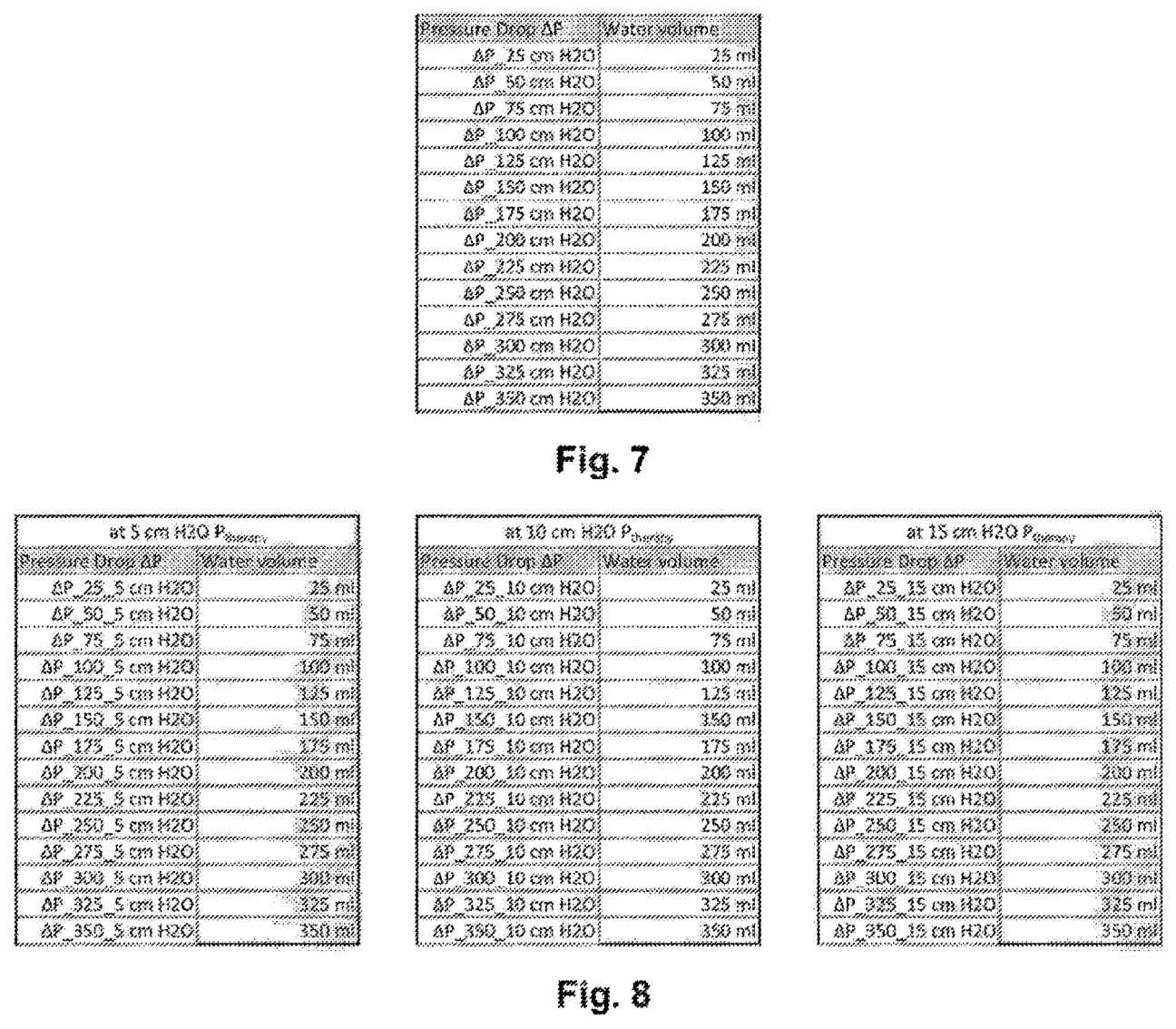

FIG. 7 shows an exemplary one-dimensional look-up table according to one aspect of the present technology.

FIG. 8 shows an exemplary two-dimensional look-up table according to one aspect of the present technology.

FIG. 9 shows an exemplary schematic of a respiratory treatment system comprising a humidifier according to one aspect of the present technology, wherein the humidifier comprises a sensor located downstream of the reservoir.

FIG. 9A shows an exemplary schematic of a respiratory treatment system comprising a humidifier according to one aspect of the present technology, wherein the humidifier comprises a pressure sensor located downstream of the reservoir.

Figure 9B:
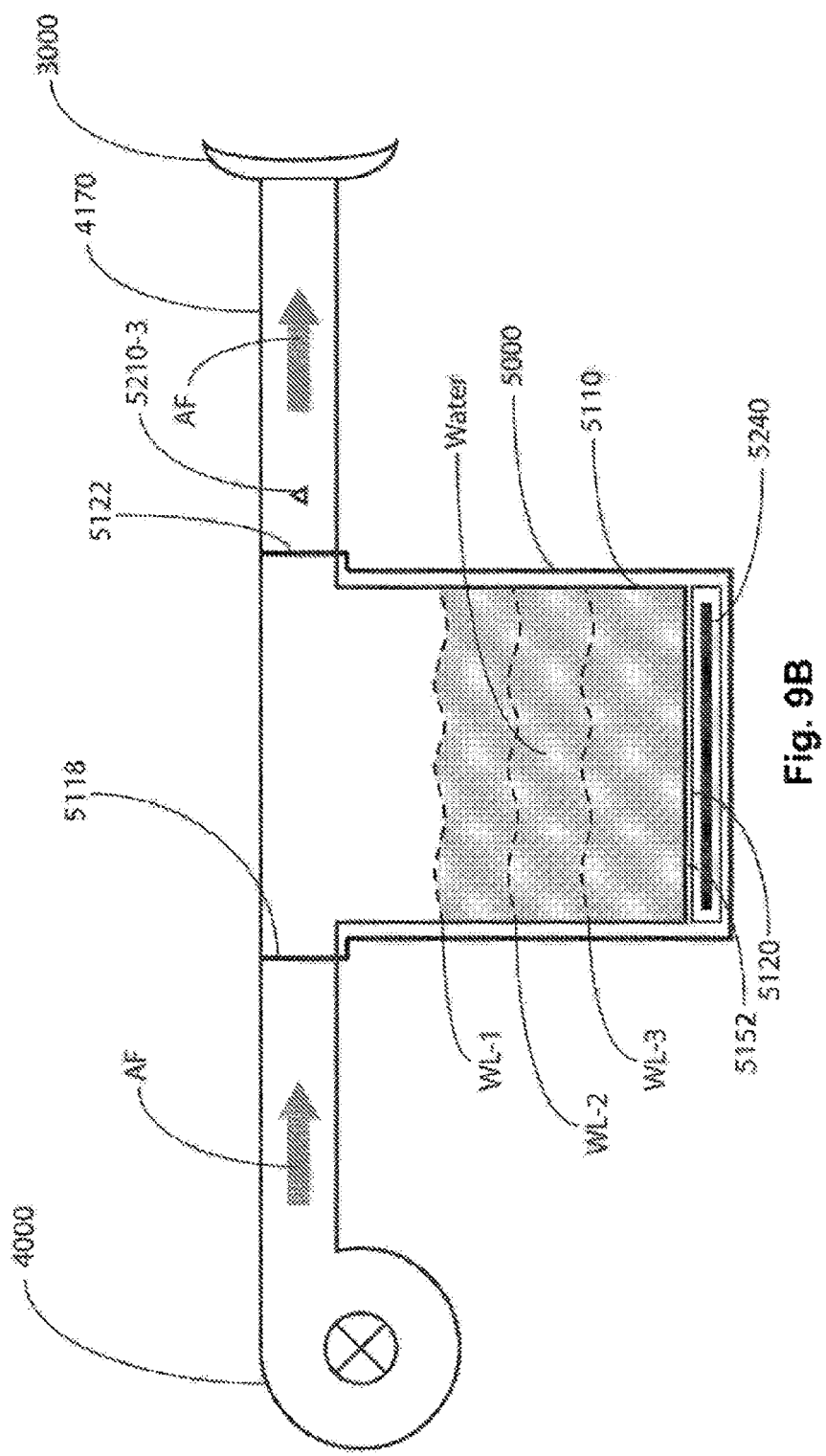

FIG. 9B shows an exemplary schematic of a respiratory treatment system comprising a humidifier according to one aspect of the present technology, wherein the humidifier comprises a flow rate sensor located downstream of the reservoir.

FIG. 9C shows an exemplary schematic of a respiratory treatment system comprising a humidifier according to one aspect of the present technology, wherein the humidifier comprises a microphone located downstream of the reservoir.

Figure 10:
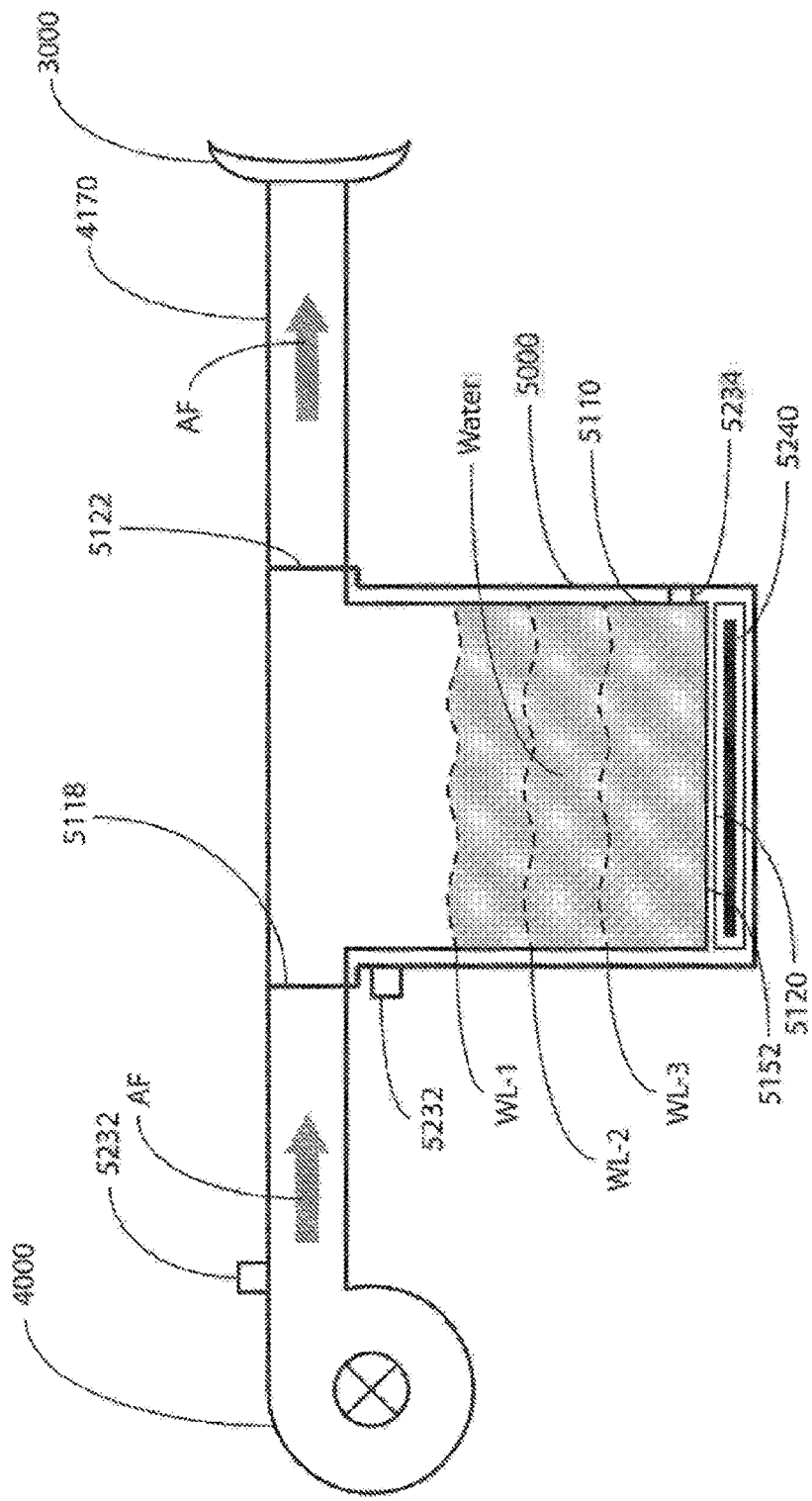

FIG. 10 shows an exemplary schematic of a respiratory treatment system comprising a humidifier according to one aspect of the present technology, wherein the respiratory treatment system comprises a vibration source and a vibration sensor.

Figure 11A:
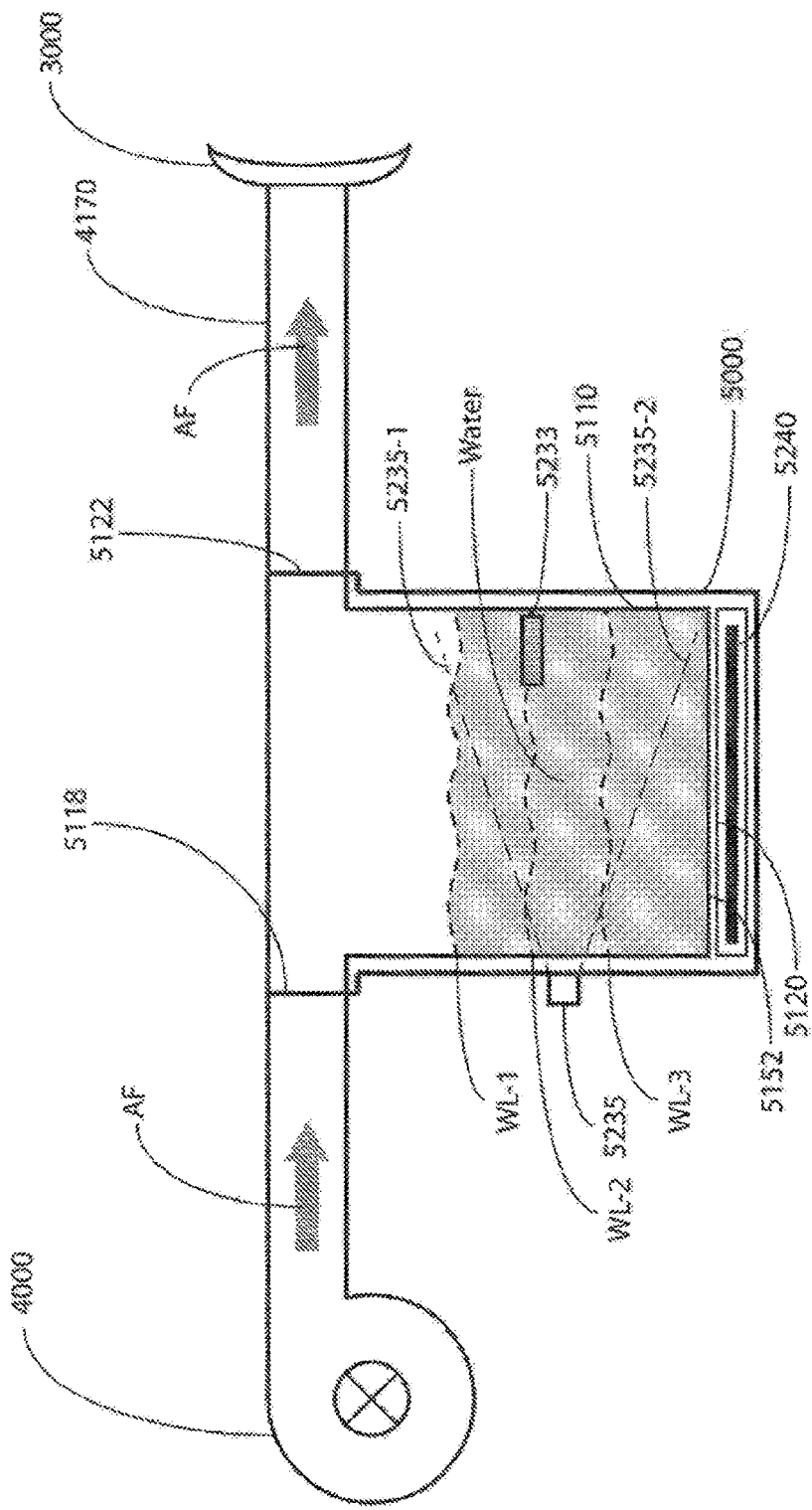

FIG. 11A shows an exemplary schematic of a respiratory treatment system comprising a humidifier according to one aspect of the present technology, wherein the respiratory treatment system comprises a movable portion and an optical sensor.

Figure 11B:
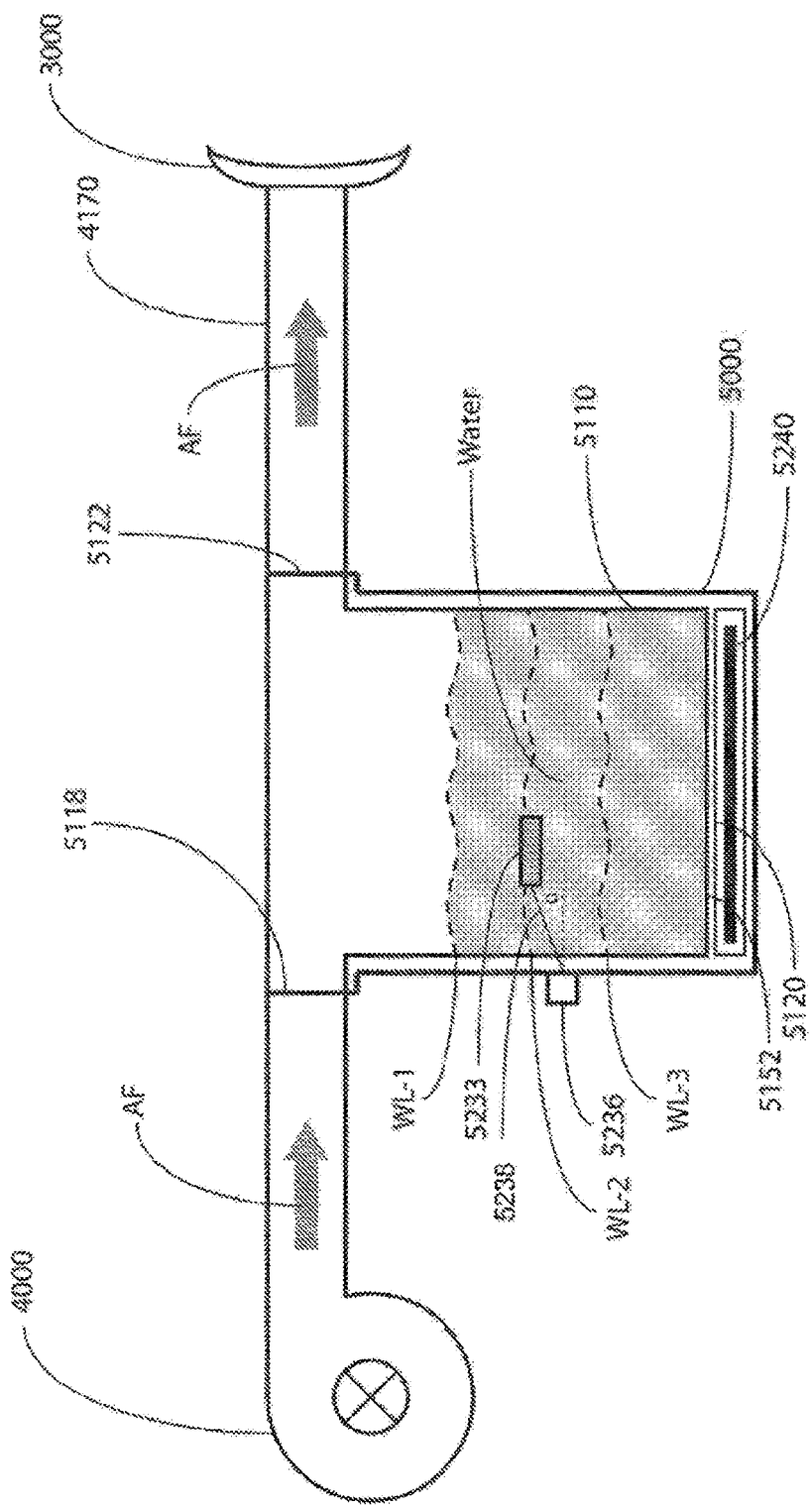

FIG. 11B shows an exemplary schematic of a respiratory treatment system comprising a humidifier according to one aspect of the present technology, wherein the respiratory treatment system comprises a movable portion and an angular sensor.

Figure 11C:
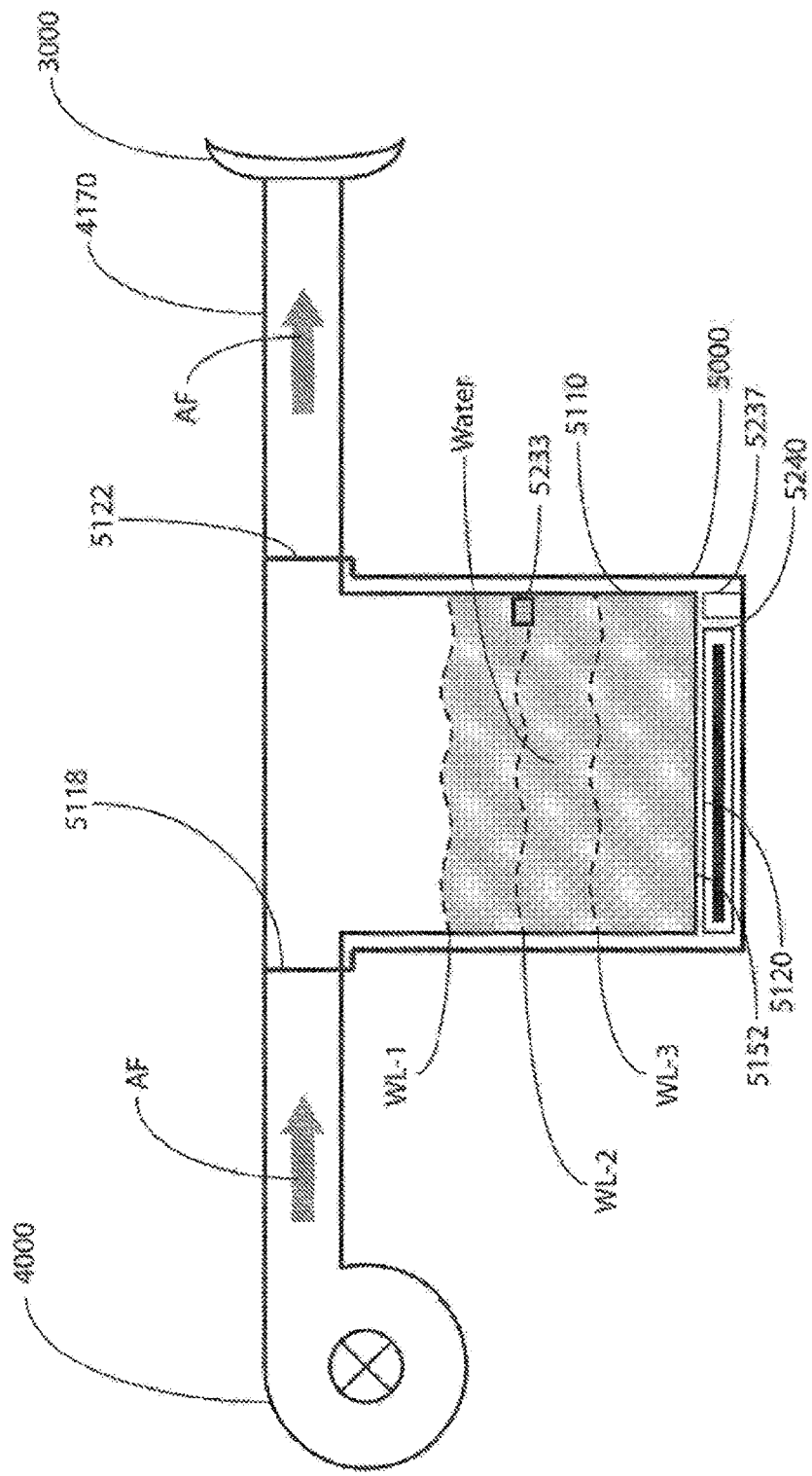

FIG. 11C shows an exemplary schematic of a respiratory treatment system comprising a humidifier according to one aspect of the present technology, wherein the respiratory treatment system comprises a movable portion and a proximity sensor.

Figure 12A:
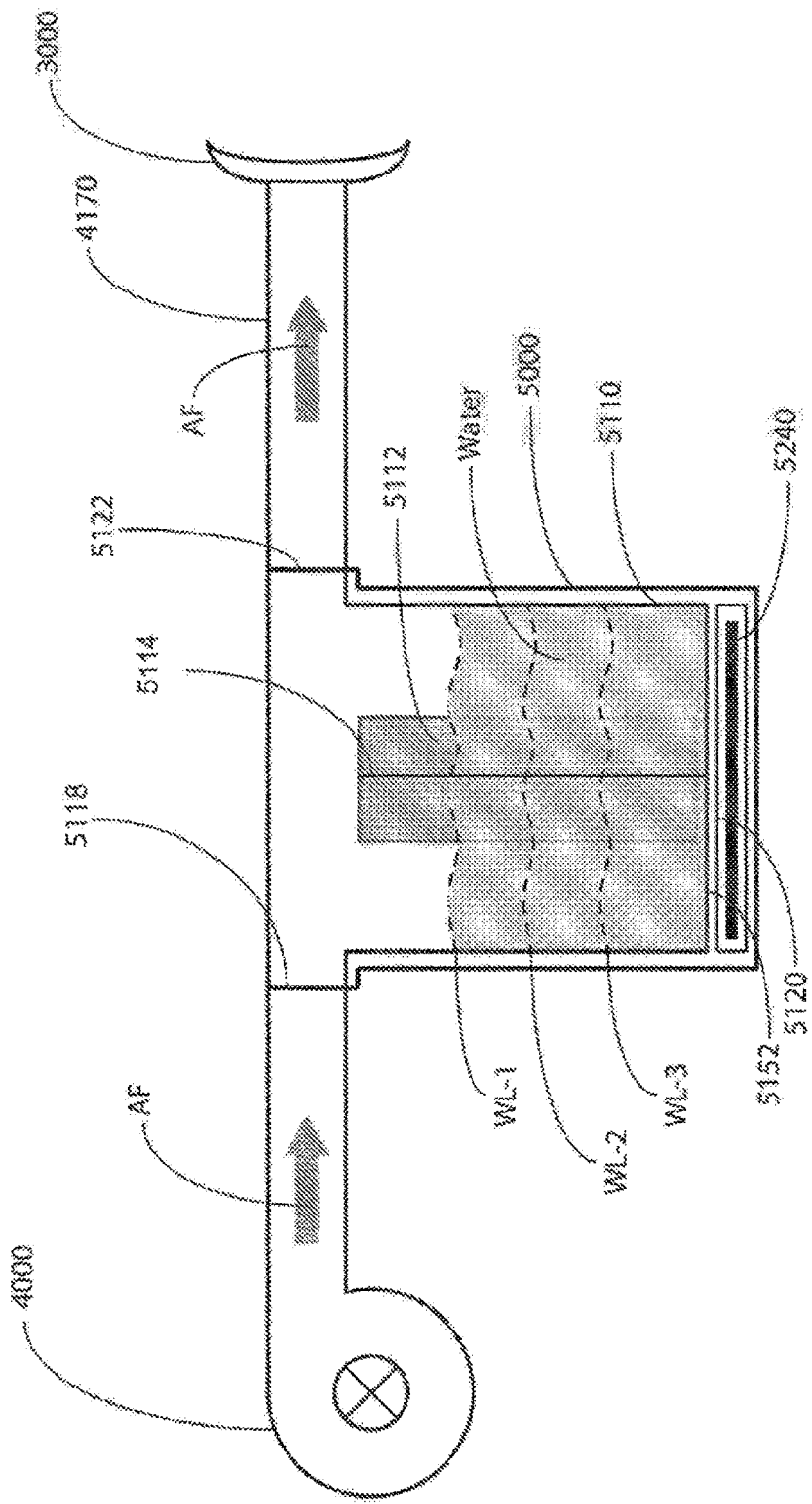

FIG. 12A shows an exemplary schematic of a respiratory treatment system comprising a humidifier according to one aspect of the present technology, wherein the humidifier comprises a rotatable paddle.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise a RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects (see FIG. 3A): a seal-forming structure 3100, a plenum chamber 3200, a positioning and stabilising structure 3300 and one form of connection port 3600 for connection to air circuit 4170. In one form, the patient interface 3000 includes a forehead support 3700. In one form, the patient interface 3000 includes a vent 3400 constructed and arranged to allow for the washout of exhaled carbon dioxide. In one form, the patient interface 3000 includes at least one decoupling structure 3500, for example, a swivel or a ball and socket. In some forms, a functional aspect may be provided by one or more physical components. In some forms, one physical component may provide one or more functional aspects. In use, the seal-forming structure 3100 is arranged to surround an entrance to the airways of the patient so as to facilitate the supply of air at positive pressure to the airways.

5.4 RPT Device

An RPT device 4000 in accordance with one aspect of the present technology (see FIGS. 4A and 4B) comprises mechanical and pneumatic components 4100, electrical components 4200, and is configured to execute one or more algorithms. The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more sensors 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, sensors 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140. See FIG. 4B.

In one form, an outlet air filter 4114, for example an antibacterial filter, is located between an outlet of the pneumatic block 4020 and a patient interface 3000. See FIG. 4B.

5.4.1.2 Muffler(s) 4120

In one form of the present technology, an inlet muffler 4122 is located in the pneumatic path upstream of a pressure generator 4140. See FIG. 4B.

In one form of the present technology, an outlet muffler 4124 is located in the pneumatic path between the pressure generator 4140 and a patient interface 3000. See FIG. 4B.

5.4.1.3 Pressure Generator 4140

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be capable of delivering a supply of air, for example at a rate of up to about 120 litres/minute, at a positive pressure in a range from about 4 $cmH_2O$ to about 20 $cmH_2O$, or, in other examples, up to about 30 $cmH_2O$. The blower may be as described in any one of the following patents or patent applications, the contents of which are incorporated herein by reference in their entireties: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g., compressed air reservoir), or a bellows.

5.4.1.4 Sensor(s)

Sensors may be internal of the RPT device, or external of the RPT device. External sensors may be located for example on or form part of the air circuit, e.g., the patient interface. External sensors may be in the form of non-contact sensors such as a Doppler radar movement sensor that transmit or transfer data to the RPT device.

In one form of the present technology, one or more sensors 4270 are located upstream and/or downstream of the pressure generator 4140. The one or more sensors 4270 may be constructed and arranged to measure properties such as a flow rate, a pressure or a temperature at that point in the pneumatic path.

In one form of the present technology, one or more sensors 4270 may be located proximate to the patient interface 3000.

In one form, a signal from a sensor 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal from the flow rate sensor 4274 is received by the central controller 4230.

Pressure Sensor 4272

A pressure sensor 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure sensor 4272 is received by the central controller 4230.

5.4.1.4.1.1 Motor Speed Sensor

In one form of the present technology, a motor speed sensor 4276 is used to determine a rotational velocity of the motor 4144 and/or the blower 4142. A motor speed signal from the motor speed sensor 4276 may be provided to the therapy device controller 4240. The motor speed sensor 4276 may, for example, be a speed sensor, such as a Hall effect sensor.

5.4.1.5 Anti-Spill Back Valve

In one form of the present technology, an anti-spillback valve 4160 is located between the humidifier 5000 and the pneumatic block 4020. The anti-spillback valve 4160 is constructed and arranged to reduce the risk that water will flow upstream from the humidifier 5000, for example, to the motor 4144.

5.4.1.6 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases, there may be separate limbs of the circuit for inhalation and exhalation. In other cases, a single limb is used.

In some forms, the air circuit 4170 may comprise one or more heating elements configured to heat air in the air circuit, for example, to maintain or raise the temperature of the air. The heating element may be in a form of a heated wire circuit, and may comprise one or more sensors, such as temperature sensors. In one form, the heated wire circuit may be helically wound around the axis of the air circuit 4170. The heating element may be in communication with a controller such as a central controller 4230 or a humidifier controller 5250. One example of an air circuit 4170 comprising a heated wire circuit is described in United States Patent Application No. US/2011/0023874, which is incorporated herewithin in its entirety by reference.

5.4.1.7 Supplemental Oxygen

In one form of the present technology, supplemental oxygen 4180 is delivered to one or more points in the pneumatic path, such as upstream of the pneumatic block 4020, to the air circuit 4170 and/or to the patient interface 3000.

5.4.2 RPT Device Electrical Components (FIG. 4D)

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, a RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control a RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS, may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more sensors 4270, and one or more input devices 4220.

The central controller 4230 may be configured to provide output signal(s) to one or more of an output device 4290, a therapy device controller 4240, a data communication interface 4280 and humidifier controller 5250.

In some forms of the present technology, the central controller 4230 is configured to implement the one or more methodologies described herein, such as the one or more algorithms expressed as computer programs stored in a non-transitory computer readable storage medium, such as memory 4260. In some forms of the present technology, the central controller 4230 may be integrated with a RPT device 4000. However, in some forms of the present technology, some methodologies may be performed by a remotely-located device. For example, the remotely-located device may determine control settings for a ventilator or may detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a control module that forms part of the algorithms executed by the central controller 4230.

In one form of the present technology, therapy device controller 4240 is a dedicated motor control integrated circuit. For example, in one form, a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology, the RPT device 4000 includes memory 4260, e.g., non-volatile memory. In some forms, memory 4260 may include battery-powered static RAM. In some forms, memory 4260 may include volatile RAM.

Memory 4260 may be located on the PCBA 4202. Memory 4260 may be in the form of EEPROM or NAND flash.

Additionally or alternatively, RPT device 4000 includes a removable form of memory 4260, for example, a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g., via Ethernet, or optical fibre) or a wireless protocol (e.g., CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Humidifier

5.5.1 Humidifier Overview

In one form of the present technology, there is provided a humidifier 5000 (e.g., as shown in FIGS. 5a, 5c and 5d) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5c and FIG. 5d, an inlet and an outlet of the humidifier reservoir 5110 may coincide with the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.5.2 Humidifier Mechanical Components

5.5.2.1 Humidifier Reservoir

According to one arrangement, the humidifier 5000 may comprise a humidifier reservoir 5110 configured to hold, or retain, a volume of liquid (e.g., water) to be evaporated for humidification of the flow of air. The humidifier reservoir 5110 is typically configured to hold a predetermined maximum volume of water in order to provide adequate humidification for at least the duration of a respiratory therapy session, such as one evening of sleep. Typically, the reservoir 5110 is configured to hold several hundred millilitres of water, e.g., 300 millilitres (ml), 325 ml, 350 ml or 400 ml. In other forms, the humidifier 5000 may be configured to receive a supply of water from an external water source such as a building's water supply system.

In one arrangement as shown in FIG. 6, the humidifier reservoir 5110 comprises an inlet 5118 configured to receive a flow of air to the interior of the humidifier reservoir 5110. The humidifier reservoir 5110 may be configured so that the flow of air may be further humidified as it passes through the interior of the humidifier reservoir 5110. The humidifier reservoir 5110 also comprises an outlet 5122 configured to deliver the humidified flow of air out of the humidifier 5000. The outlet 5122 may be connected to an air circuit 4170 through which the humidified flow of air may be delivered to the patient 1000 via the patient interface 3000. In one form, the humidifier reservoir 5110 may be configured to encourage the flow of air to travel in a tortuous path through the reservoir 5110 while in contact with the volume of water therein, in order to maximize the surface area of the water that the air contacts as it travels between the inlet 5118 and the outlet 5122.

According to one form, the reservoir 5110 may be removable from the humidifier 5000, for example, in a horizontal direction as shown in FIGS. 5C and 5D.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.5.2.2 Conductive Portion

According to one arrangement, the reservoir 5110 comprises a conductive portion 5152 configured to allow efficient transfer of heat from the heating element 5240 to the volume of liquid in the reservoir 5110. In one form, the conductive portion 5152 may be arranged as a plate, although other shapes may also be suitable. All or a part of the conductive portion 5152 may be made of a thermally conductive material such as aluminium (e.g., approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

The conductive portion 5152 may be coupled with a heating element 5240 to introduce heat to the interior of the humidifier reservoir 5110. Humidifier reservoir dock In one form, the humidifier 5000 may comprise a humidifier reservoir dock 5130 (as shown in FIG. 5D) configured to receive the humidifier reservoir 5110. In some arrangements, the humidifier reservoir dock 5130 may comprise a locking feature such as a locking lever 5135 configured to retain the reservoir 5110 in the reservoir dock 5130.

5.5.2.3 Water Level Reference

The humidifier reservoir 5110 may comprise a water level reference 5150 as shown in FIG. 5C-5D. In some forms, the water level reference 5150 may provide one or more references to a user such as the patient 1000 or a care giver regarding a quantity of the volume of water in the humidifier reservoir 5110. The one or more references provided by the water level reference 5150 may include an indication of a maximum, predetermined volume of water, and/or any portions thereof, such as 25%, 50% or 75% or volumes such as 200 ml, 300 ml or 400 ml.

5.5.2.4 Heating Plate 5120

According to another aspect of the present technology, the humidifier 5000 may comprise a heating plate 5120 that is used to transfer heat to the humidifier reservoir 5110 as shown in FIG. 6. The heating plate 5120 may comprise a heating element 5240 located on or near the base of the humidifier 5000. In one form, the heating plate 5120 may simply cover a heating element 5240. The heating plate 5120 may be formed, for example, of a nickel chrome alloy, stainless steel or anodised aluminium.

5.5.3 Humidifier Electrical & Thermal Components (FIG. 5B)

The humidifier 5000 may comprise a number of electrical and/or thermal components such as those listed below.

5.5.3.1 Humidifier Sensor(s)

The humidifier 5000 may comprise one or more humidifier sensors (e.g., transducers) 5202 instead of, or in addition to, sensors 4270 described above. Humidifier sensors 5202 may include one or more of a pressure sensor 5205, a flow rate sensor 5210, a temperature sensor 5220, or a humidity sensor 5218 as shown in FIG. 5B. A humidifier sensor 5202 may produce one or more output signals which may be communicated to a controller such as the central controller 4230 and/or the humidifier controller 5250. In some forms, a humidifier sensor may be located externally to the humidifier 5000 (such as in the air circuit 4170) while communicating the output signal to the controller. The term 'sensor' will be taken to include one or more transducers in the present document unless otherwise explicitly stated. Such an externally located sensor can permit implementation of a replaceable humidifier reservoir (e.g., container) that does not also require replacement or removal of the sensor (e.g., the sensor is not directly coupled to the container).

5.5.3.1.1 Pressure Sensor

One or more pressure sensors 5205 may be provided to the humidifier 5000 in addition to, or instead of, a pressure sensor 4272 provided to the RPT device 4000.

5.5.3.1.2 Flow Rate Sensor

One or more flow rate sensors 5210 may be provided to the humidifier 5000 in addition to, or instead of, a flow rate sensor 4274 provided to the RPT device 4000.

5.5.3.1.3 Temperature Sensor

The humidifier 5000 may comprise one or more temperature sensors 5220. The one or more temperature sensors 5220 may be configured to measure one or more temperatures, such as the temperature of the heating element 5240 and/or the temperature of the flow of air through the humidifier (e.g., in the humidifier 5000 and/or downstream of the humidifier outlet 5004). In some forms, the humidifier 5000 may further comprise a temperature sensor 5220 configured to detect the temperature of the ambient air.

5.5.3.1.4 Humidity Sensor

In one form, the humidifier 5000 may comprise one or more humidity sensors 5218 to detect a humidity of a gas, such as the ambient air. A humidity sensor 5218 may be placed near the humidifier outlet 5004 in some forms to measure a humidity of the gas delivered out of the humidifier 5000. Each humidity sensor may be an absolute humidity sensor or a relative humidity sensor.

5.5.3.2 Heating Element

A heating element 5240 may be provided to the humidifier 5000 in order to provide a heat input to liquid and/or gas therein. For example, the heating element 5240 may provide a heat input to one or more of: the volume of water in the humidifier reservoir 5110; and the flow of air through the humidifier. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5D. According to one arrangement, the heating element 5240 may be moulded into a resin forming a tub, as disclosed in the PCT patent application WO 2008/148154, the contents of which is incorporated herein by reference.

5.5.3.3 Humidifier Controller

According to one arrangement of the present technology, a humidifier 5000 may comprise a humidifier controller 5250. In one form, the humidifier controller 5250 may be a part of the central controller 4230. In another form, the humidifier controller 5250 may be a separate controller, which may be in communication with the central controller 4230 as shown in FIG. 4C.

In one form, the humidifier controller 5250 may receive as inputs measurements of properties (such as temperature, humidity, pressure and/or flow rate), for example, of the flow of air, and/or of the water in the reservoir 5110 and/or the humidifier 5000. The humidifier controller 5250 may also be configured to execute or implement humidifier algorithms and/or deliver one or more output signals.

As shown in FIG. 5B, the humidifier controller may comprise one or more controllers, such as a central humidifier controller 5251, a heated air circuit controller 5254 configured to control the temperature of a heated air circuit 4170, and/or a heating element controller 5252 configured to control the temperature of a heating element 5240. In some cases, humidifier algorithms may also utilize outputs from one or more sensors.

5.5.3.4 Water Quantity (Level/Volume) Determination

As discussed in further detail above, the humidifier reservoir 5110 may contain a body of liquid, such as water, which is evaporated to add humidity to the flow of air travelling through the humidifier 5000. In some cases, it may be desirable to determine the quantity of liquid that is present in a humidifier reservoir 5110. It is noted that where references are made to determination of 'water quantity', it is to be understood that such techniques are not to be limited to applications in determining a quantity of water, but would also be applicable to other liquids. It may be desirable for the humidifier 5000 to self-monitor the quantity of water in the reservoir 5110 without active monitoring by a user/person. For example, if the user is visually impaired or incapacitated, the user may be unable to visually inspect the quantity of water in the reservoir 5110. Also, it may be difficult for a user to determine the height of water in the reservoir 5110 if the reservoir is opaque, or if the room where the humidifier 5000 is located is darkened for the user to relax or eventually sleep.

In some forms, it may be desirable to determine the quantity of water in the reservoir 5110 by indirect measurements, such as without sensing a water level by detecting its height with a mechanical float. For example, indirect measurements of the quantity of water may allow determination of the water quantity without use of sensors that form a part of a disposable component such as the reservoir 5110. Furthermore, indirect measurements of the quantity of water may be carried out using sensors that may have other functions, such as control of temperature and/or pressure (e.g., therapy pressure) of the air flow delivered to the patient, which may lead to improved efficiency and/or lower cost. Indirect measurements of water quantity are described in further detail below. Thus, in some cases, a dedicated sensor(s) may be implemented for the detection of water quantity. However, in some cases, the sensor(s) involved in other standard control functions of an RPT device (e.g., pressure control or flow sensing etc.) may be additionally tasked to serve the different purpose of water quantity sensing.

The quantity of water may be determined and/or processed in terms of any number of units, relative or absolute. For example, the quantity of water may be measured in a unit of volume, such as litres, millilitres or cubic centimeters, in a unit of mass such as in grams, kilograms or ounces, in relative measurements such as a percentage or a fraction of the maximum recommended fill level, in any arbitrary units such as a number out of five or a number out of 10, where the maximum number represents the maximum recommended fill level, and in some cases by a measurement of the size of the void (e.g., the quantity of air) in the reservoir 5110. In some forms, the water quantity may be expressed as a 'level' to indicate a height, however it will be understood that a reference to any particular form of measurement (e.g., water level, water volume or water mass) is not intended to be limiting to the express form. Thus, in some cases the determined reservoir water quantity may be expressed as an amount of water needed to fill the humidifier given the amount of water present in the humidifier or it may be expressed as the amount of water present in the humidifier.

5.5.3.4.1 Use of Determined Water Quantity

One advantage associated with being able to determine the quantity of water present in the reservoir 5110 may be in being able to inform, or alert a user, such as a caregiver or a patient 1000, of the determined water quantity. Additionally, or alternatively, the user may be informed or alerted based on other information which may be inferred from the determined water quantity. According to one aspect of the present technology, the patient 1000 may be alerted of a low water quantity prior to commencement of a therapy session. For example, the patient may be alerted if the determined water quantity is below a predetermined threshold level. In some cases, the alert may identify by estimate of how much time or number of sessions of use of the RPT will remain before additional water will be needed. Such an estimate may be based on historic water depletion data (e.g., recorded time of use and quantity of water depleted, rate of water depletion, etc.) given a patient's RPT use.

According to another such aspect, a controller may determine whether the determined water quantity may be sufficient for humidification of air flow throughout a remainder of a therapy session. In one form, the user may be prompted to refill the reservoir 5110 before commencing therapy. In one form, the user may be alerted upon completion of therapy to refill the reservoir 5110 if the determined water quantity may not be sufficient for humidification of air throughout the entirety of another therapy session.

According to another aspect, an alarm may be activated when the reservoir 5110 is out of water, or when the water level is determined to be low (e.g., below a threshold). An alarm may be activated at any time, such as prior to commencement of a therapy session, at the completion of a therapy session, or during a therapy session. In one form, a controller such as a central controller 4230 or the humidifier controller 5250 may activate an alarm. In some cases where the patient 1000 requires humidified air and may not be able to refill the reservoir 5110 without assistance, the alarm may alert a caregiver (e.g., a nurse) that refilling is required, such as by transmission of an alert message via a communications device (e.g., email, pager message, short message service (SMS) message, etc.).

In another form, determination of water quantity in the reservoir 5110 may allow for a humidification output to adapt to the available water quantity and/or the rate of water usage, as will be described below in further detail.

In some arrangements, the reservoir 5110 may be disposable and may require replacement (e.g., periodically, based on usage or for individual patients) throughout a life of the humidifier 5000. In such arrangements, the introduction of any additional components into the reservoir 5110, such as a sensor, may not be desirable, as this may increase the cost of the disposable reservoir 5110, particularly if the additional components are relatively expensive. Yet further, in order to introduce a sensor into the reservoir 5110, which may be removable from the humidifier 5000, one or more electrical connections that can be coupled and uncoupled may be required between the humidifier reservoir 5110 and other components such as the humidifier controller 5250 and/or a power source (e.g., power supply 4210). The presence of such electrical connections that can be coupled and uncoupled may also not be preferable, as they may increase system complexity, increase the cost of the disposable reservoir 5110, and introduce potential failure points in a disposable component.

Thus, it may be preferable to determine a quantity of water in a humidifier reservoir 5110 using one or more sensors that do not form a part of the reservoir 5110 (i.e., not a component of the disposable/replaceable portion of the humidifier system). Furthermore, it may be preferable to determine the water quantity using the sensors that may also be used in a humidifier 5000 and/or an RPT device 4000, for example, to measure one or more properties of the air flow.

5.5.3.4.2 Determination of Effects of Varying Water Quantity

According to some arrangements of the humidifier reservoir 5110 according to the present technology, a variation in the quantity of water present in the humidifier reservoir 5110 may affect one or more measurable characteristics or properties, such as those of: the water, the flow of air, the reservoir 5110 and/or the humidifier 5000. The characteristic(s) or property(s) affected by a variation in the quantity of water (and thus may be used to infer the quantity of water) may include, but not be limited to, pressure, flow rate, noise, temperature or vibration. These characteristics will be referred to hereafter as indicative characteristics. A person skilled in the art would understand given the present specification that there may be other, similar, characteristics to those 'indicative characteristics' disclosed in the present document, which may also be used to determine a water quantity in the reservoir 5110 in a manner substantially equivalent to those disclosed herewithin.

Thus, one or more measurements of one or more indicative characteristics may be used to determine the quantity of water in the reservoir 5110. A quantity of water may be determined for a particular time, or a change in the quantity of water in the reservoir 5110 between a first time and a second time may be determined. For example, a measurement of the indicative characteristic may be used as a variable in a look-up table or in a function to determine an estimate of the quantity of water in the reservoir 5110 or the change in the quantity of water in the reservoir 5110 between two points in time.

As will be described in further detail below, a measurement of an indicative characteristic may be a measurement of an aspect of the indicative characteristic, such as a magnitude or a direction of a vector quantity. For example, where a noise is an indicative characteristic, a measurement of an indicative characteristic may be a measurement of amplitude of the noise, a measurement of phase of the noise, or a combination of both aspects.

In some forms, each 'measurement' herein may in fact refer to a set of measurements (one or more measurements or values derived from one or more sensors), such that for example a first set of measurements and a second set of measurements may be used to determine the quantity of water.

In one form, a plurality of measurements such as a first measurement and a second measurement of the indicative characteristic(s) may be used to determine the quantity of water. The plurality of measurements may be of one indicative characteristic or a plurality of indicative characteristics. For example, a measurement of pressure of the flow of air from a pressure sensor and a measurement of flow rate of the flow of air from a flow rate sensor may be used to determine the quantity of water.

The plurality of measurements may be obtained from a single sensor, or a plurality of sensors. As an example, a first microphone may measure a first measurement of noise and a second measurement of noise. Or, a first microphone and a second microphone may respectively measure a first measurement of noise and a second measurement of noise. The first measurement of noise and the second measurement of noise may then be used to determine the quantity of water in the reservoir. In another form, one measurement of an indicative characteristic may be used to determine the water quantity in the reservoir 5110. For example, a single measurement of noise from a microphone may be used to determine the quantity of water.

The measurement system may generate a reference signal such as a waveform (e.g., with a predetermined shape, frequency and/or amplitude), or an impulse, for use in determination of water quantity. To this end, the measurement system may comprise a reference generator configured to generate the reference signal, such as a loudspeaker or the blower 4142. In some forms, the reference signal may be measured by one or more sensors to determine a reference data set, to which a measurement set may be compared to determine a quantity of water. A measurement set may be determined (e.g., second measurement set measured) after at least a predetermined length of time has passed subsequent to the reference data set (e.g., first measurement set).

In some forms, the reference data set may be determined from estimation, whereby water quantity may be determined from a resulting measurement set (e.g., from a single sensor 5202-3 as shown in FIG. 9) and the estimated reference data set. For example, a reference data set may include an estimated pressure based on a measurement of motor speed. In one form, a time taken for a reference signal (e.g., airflow, sound or noise) to travel from the reference generator, through the reservoir 5110, and to the sensor may be measured to determine a time lag. Yet further, any transformation, such as a phase change, or a change in amplitude, that the reference signal undergoes prior to arriving at the sensor, may then be measured and used to infer the volume of water in the reservoir 5110.

Further details of determination of the quantity of water in the reservoir 5110 by use of indicative characteristics will be discussed below.

5.5.3.4.3 Measurements of the Air Flow

According to one aspect of the present technology, a quantity of water in the reservoir 5110 may be determined from a measurement set (one or more measurements) of the air flow, for example as measured in the reservoir 5110 or downstream of the reservoir 5110. As used herein, a measurement or a measurement set may comprise a single measured value from a sensor, or a plurality of measured values from a sensor. In one example, a plurality of measured values from a sensor may be averaged over a short period of time to determine an average value of a particular characteristic over the short period of time. In such an example, by averaging a plurality of measured values from a single sensor, the measurement from the sensor may be used to more accurately determine the water volume in the reservoir 5110, such as if, for example, a user accidentally jostles the reservoir 5110 during sensing of the values from the sensor. In another example, a plurality of measured values from a sensor may be filtered (e.g., using a low-pass signal filter) to determine a representative value of a particular characteristic over a period of time.

A property of the reservoir 5110 and the water contained therein, such as its acoustic transmission loss, flow impedance, thermal mass or thermal conductivity, may vary according to the quantity of water present in the reservoir 5110. In turn, one or more characteristics of the flow of air that travels through the reservoir 5110 may be affected, such as pressure, flow rate, temperature, noise, or vibration. Thus, the affected characteristic(s) of the air flow may indicate the quantity of water in the reservoir 5110 when measured in the reservoir 5110 or downstream of the reservoir 5110, and in some cases, when measured upstream of the reservoir 5110. For example, a decrease in the quantity of water in the reservoir 5110 may decrease the overall thermal mass of the reservoir 5110.

FIG. 6 shows an arrangement of a system according to the present technology that comprises a first sensor 5202-1 and a second sensor 5202-2. Three exemplary, possible quantities of water in the reservoir 5110 are indicated by three water levels WL-1, WL-2 and WL-3 in FIG. 6. An exemplary travel path for the flow of air through the reservoir 5110 is indicated by the arrows AF.

The flow of air may undergo a pressure drop (e.g., a decrease in static or total pressure) as it travels through the reservoir 5110, for example, as measured between the reservoir inlet 5118 and the reservoir outlet 5122. A magnitude of the drop in pressure of the flow of air may vary according to a flow impedance of the reservoir 5110. As the quantity of water in the reservoir 5110 is varied, the flow impedance of the reservoir 5110 may be altered due to a change in a path for the air flow through the reservoir 5110 as the effective boundaries of the reservoir 5110 change (e.g., from WL-1 to WL-2 in FIG. 6). As a result, a difference between the air pressure at the reservoir inlet 5118 and at the reservoir outlet 5122 may be affected by the change in the quantity of water in the reservoir 5110. Thus a pressure of the flow of air may be a suitable indicative characteristic of the quantity of water present in the reservoir 5110.

Similarly, any number of properties of the flow of air may be suitable indicative characteristics of the quantity of water present in the reservoir 5110. Suitable indicative characteristics of the flow of air may include pressure, flow rate, temperature, density, noise or vibration or other characteristics of the flow of air. Thus, one or more of the indicative characteristics may be measured from the air flow to determine the quantity of water in the reservoir 5110.

According to the arrangement shown in FIG. 6, the first sensor 5202-1 may determine a first measurement set M1 of an indicative characteristic of the flow of air, and the second sensor 5202-2 may determine a second measurement set M2 of an indicative characteristic the flow of air. The first measurement set M1 and the second measurement set M2, and/or their relationship, such as a difference in amplitude, or a difference in phase, may then be correlated to a quantity of water in the reservoir 5110 using a function or a look-up table, as will be discussed in more detail below.

Locations of the sensor(s) need not be limited to the particular exemplary locations discussed herein in order to take advantage of the present technology as disclosed. Examples of suitable locations for the sensor(s) may include the inlet or the outlet of the RPT device 4000, the inlet or the outlet of the humidifier 5000, the interior of the reservoir 5110, the interior of the air circuit 4170, the interior of the patient interface 3000, or other locations in fluid communication with the flow of air. In some cases, the sensor(s) may be located between or near any of the above listed components. In one arrangement, at least a part of the reservoir 5110 is located between at least two sensors when a plurality of sensors is employed.

Referring to FIG. 6, the first sensor 5202-1 is shown at a first location, upstream of the reservoir 5110, and the second sensor 5202-2 is shown at a second location, downstream of the reservoir 5110. Alternatively, the sensors 5202-1 and/or 5202-2 may be arranged as shown in FIG. 6C, where the first sensor 5202-1 is located within the reservoir 5110 and the second sensor 5202-2 is located proximal to the patient interface 3000. A sensor may be integrally formed with another component such as the RPT device 4000, an air circuit 4170 or the humidifier 5000 (or a sub-component thereof). In other arrangements, a sensor may be removably connected to another component.

In an arrangement of the present technology as shown in FIG. 6A, a first pressure sensor 5205-1 and a second pressure sensor 5205-2 may each determine measurements of pressure of the flow of air. The first pressure sensor 5205-1 may determine a first measurement of pressure $P_m1$ of the flow of air at a first location, and the second pressure sensor 5205-2 may determine a second measurement of pressure $P_m2$ of the flow of air at a second location. A measurement of pressure drop $\Delta P_m$ between the first location and the second location may be determined using the formula $\Delta P_m = P_m1 - P_m2$. The measurement of pressure drop $\Delta P_m$ may then be used to determine the quantity of water in the reservoir (e.g., as shown in FIG. 7) as described in further detail below.

In an illustrative example, a maximum allowable quantity (in volume) of water in the reservoir 5110 may be approximately 350 ml. In FIG. 6, the corresponding water level may be WL-1. When the water volume is 350 ml, at a therapy pressure (i.e., a pressure at the patient interface 3000) of 10 cm $H_2O$, a first measurement of pressure $P_m1$ at the first pressure sensor 5205-1 may be called $P_m1_{350}$ and a second measurement of pressure $P_m2$ at the second pressure sensor 5205-2 may be called $P_m2_{350}$. Based on the first measurement of pressure $P_m1_{350}$ and the second measurement of pressure $P_m2_{350}$, a measurement of pressure drop at 350 ml of water $\Delta P_{m350}$ may be calculated using the following formula $\Delta P_{m350} = P_m1_{350} - P_m2_{350}$. However, if the water volume was to decrease to 240 ml for instance, it may lower the water level to WL-2, increasing the effective internal volume of air in the reservoir 5110. In this case, the measurement of pressure drop may change to $\Delta P_{m240}$, and similarly at 130 ml of water volume at water level WL-3, the measurement of pressure drop may then change further to $\Delta P_{m130}$. Thus the quantity of water may be determined based on the measurement of pressure drop.

In some forms, the quantity of water in the reservoir may be determined based on the measurement of pressure drop $\Delta P_m$, using one or more functions and/or look-up tables. An example of a look-up table is shown in FIG. 7, where a series of pressure drop values (measured in pressure) are correlated (such as by numerical, experimentation or empirical analysis) to water quantity values (measured in volume). According to one arrangement, a memory 4260, in communication with the controller, may store the data of the look-up tables (and/or functions). The controller may receive the measurement of pressure drop $\Delta P_m$ as an input and determine the water quantity based on the look-up table (and/or functions). In one example, the look-up tables may be customized or adapted by a calibration and/or self-learning process of a controller of humidifier 5000. For example, different fluid levels may be identified by a user in response to a prompt of the controller and pressure drops (or other values) may be calculated and associated with the identified levels.

In some forms, the controller may be configured to determine the water quantity from the closest value of pressure drop available $\Delta P$ in the look-up table to the measurement of pressure drop $\Delta P_m$. For instance, in the look-up table shown in FIG. 7, the closest pressure drop value $\Delta P$ to the measured pressure drop at 350 ml of water $\Delta P_{m350}$ may be $\Delta P\_350$, and the determined water volume may be 350 ml. Or, the closest pressure drop value $\Delta P$ to the measured pressure drop at 240 ml of water $\Delta P_{m240}$ may be $\Delta P\_250$, and the determined water volume may be 250 ml Alternatively, the controller may be configured to interpolate between listed values in the look-up table by any suitable interpolation methods such as linear, polynomial, piecewise constant interpolation or a combination thereof. Using interpolation, two closest values of pressure drop $\Delta P$ to the measured pressure drop at 240 ml of water $\Delta P_{m240}$ may be $\Delta P\_250$ and $\Delta P\_225$, and the controller may determine the quantity of water by interpolating between the two values.

In one form, a look-up table may be multi-dimensional as shown in FIG. 8. This may allow effects of any one or more additional variables (such as therapy pressure ($P_{therapy}$), pressure at pressure generator, pressure generator motor speed, pressure generator motor current, flow rate, length of air circuit 4170, type of humidifier reservoir 5110 or other indicative characteristics) to be taken into consideration when determining the water quantity.

In one form, the look-up table may be populated by a manufacturer by characterisation of the reservoir 5110 and stored in a memory (e.g., in the RPT device 4000 or humidifier 5000). Additionally, or alternatively, the humidifier controller 5250 may also comprise the ability to calibrate and populate the look-up table by using a learn mode during therapy, and/or by executing or performing a calibration cycle, both of which will be described in further detail below.

In one form, the quantity of water may be determined from measurements of indicative characteristic(s) based on one or more functions. The one or more functions may be predetermined and made available to a controller such as the humidifier controller 5250, for example stored in a memory (e.g., in the RPT device 4000 or humidifier 5000). In some forms, the function correlating the indicative characteristic(s) to the quantity of water may be selected from a plurality of functions, for example, according to a variable (e.g., therapy pressure). Alternatively, or additionally, the function may be calibrated by a learn mode during therapy or by performing a calibration cycle. Thus, in one example, the function may determine the quantity of water, in volume $V_w$ based on a measurement of the pressure drop $\Delta P_m$, using a linear equation $V_w = A \times \Delta P_m + B$, where A and B are values that may be predetermined and/or adjusted by calibration/learn mode. The function may also take one or more of any number of suitable forms, such as a linear, polynomial, logarithmic or a combination thereof.

FIG. 9 shows an arrangement of a system that comprises a sensor 5202-3. In this arrangement, a measurement M3 determined by the sensor 5202-3 may be used as an input to a look-up table or a function to determine the quantity of water in the reservoir 5110. In another example, a reference value $M_{ref}$ may be used to compare to the output or the measurement M3 produced by the sensor 5202-3 to determine the quantity of water. The reference value $M_{ref}$ may be a fixed and/or a predetermined value. The reference value $M_{ref}$ may additionally or alternatively be determined from another characteristic such as a motor speed, motor current, ambient temperature, ambient pressure or ambient density among others. For example, density of the air through the device may be measured, from which temperature of the air may be inferred, from which temperature of the water may be inferred and from which a volume of water or the reservoir may be estimated. Yet further, the reference value $M_{ref}$ may be based at least partly on a previous measurement determined by the sensor 5202-3.

In the exemplary arrangement shown in FIG. 9A, a pressure sensor 5205-3 is located downstream of the humidifier reservoir 5110, and the pressure sensor 5205-3 may determine a measurement of pressure $P_m 3$. The measurement of pressure $P_m 3$ may be used as an input to a look-up table or a function to determine the quantity of water. Alternatively, or additionally, the measurement of pressure $P_m 3$ may be compared to a reference pressure $P_{ref}$, for example to produce an estimated pressure drop $\Delta P_e = P_{ref} - P_m 3$ (where $P_{ref}$ is upstream of $P_m 3$). A look-up table or a function may be used to determine the quantity of water based on the estimated pressure drop similarly to the method described above. The reference pressure may be predetermined, or variable, for example the reference pressure may be estimated from parameters such as motor current, motor speed, motor acceleration and/or altitude as disclosed in PCT Application Number PCT/AU2013/000695 for example, the entire contents of which is enclosed herewithin by reference. In a yet another alternative, the measurement of pressure $P_m 3$ may be used as an input to a look-up table or a function, wherein the look-up table or the function may vary according to the reference pressure $P_{ref}$.

In some forms, the quantity of water in the reservoir 5110 may be determined from a plurality of measurements of indicative characteristics over time. For example, measurements of indicative characteristics over time may include effects of one or more breath waveforms, such as inspiratory or expiratory waveforms. Characteristics of the flow of air such as its pressure, flow rate or temperature may be affected due to breathing of the patient 1000. For example, when the patient 1000 breathes out, the air pressure may increase, including at or near the humidifier reservoir 5110. When the patient 1000 breathes in, the air pressure may decrease, including at or near the humidifier reservoir 5110. A magnitude of a variation of the indicative characteristics (such as pressure) may depend on a quantity of water in the reservoir 5110. The effect that the patient's breathing has to the characteristics of the flow of air may thus be measured to determine the quantity of water in the reservoir 5110. In some cases, detection of patient breathing cycle, e.g., expiration, inspiration or parts thereof, may trigger timing of particular measurements for water level detection. For example, a measurement may be synchronized for a particular phase of the patient's respiratory cycle (such as the start of expiration or the start of inspiration) so as to assist with controlling for changes to the system that may be influenced by the patient's breathing cycle.

In another example, one or more of a patient's breath waveforms (or a part thereof), such as inspiratory or expiratory waveforms may be determined using an arrangement as shown in FIG. 9B. For instance, a difference in flow rates between expiration and inspiration at a flow rate sensor 5210-3 may be determined by producing a measurement of maximum flow rate and a measurement of minimum flow rate over a breath cycle. The difference in flow rates may then be calculated as the difference between the measurement of maximum flow rate and the measurement of minimum flow rate over a breath cycle. The water level may then be determined by correlation to, for example, the difference between flow rate between expiration and inspiration.

In one arrangement of the present technology, the central controller 4230 of the RPT device 4000 may be configured to maintain the blower 4142 at a fixed speed for each target therapy pressure. According to this arrangement, a change in flow impedance of the reservoir 5110 may affect the flow rate of air through the air circuit, as the blower 4142 operates at a constant speed.

FIG. 9B shows one arrangement of a system that may be suitable for determining the quantity of liquid in the reservoir 5110 using a flow rate sensor 5210-3 when such a constant-speed blower is used. The flow rate sensor 5210-3 may produce a measurement of the flow rate $F_m3$, which would vary as the flow impedance of the reservoir 5110 varies. Accordingly, the measurement of the flow rate $F_m3$, as well as a speed of the blower 4142 may be correlated to determine the quantity of water in the reservoir 5110, such as, by using a two-dimensional look-up table or a two-variable function. In some cases, other characteristics, such as motor current or altitude may be added as independent dimensions or variables to the look-up table and/or the function to further improve accuracy of the look-up table of the function.

According to a yet another aspect of the present technology, noise may be a suitable indicative characteristic from which the quantity of water may be determined. For example, a sensor may be placed to determine a measurement of noise at a location where the noise may be affected by the quantity of water in the reservoir 5110. Suitable locations may include: in the reservoir 5110 or downstream of the reservoir 5110 such as in the humidifier 5000, in the air circuit 4170 or the patient interface 3000. The resulting noise may be used to determine the quantity of water remaining in the reservoir 5110, for example by a comparison to a measured or estimated reference noise.

In some cases, the reference noise may be a noise output by a reference generator, which may be a component of the RPT device 4000 and/or the humidifier 5000. For example, noise created by the blower 4142 as a by-product of generating a pressured flow of air may be used as the reference noise. In this case, the level and frequency characteristics of the reference noise may therefore vary (e.g., according to a pressure or flow rate delivered by the blower 4142), and may need to be measured (or estimated) in conjunction with the resulting noise to establish a relationship therebetween. Alternatively, or additionally, the reference noise input may include a known noise output from a component such as a speaker or a buzzer. According to another feature of the present technology, the measurement of the resulting noise may include a filter to exclude or reduce the effects of other noise sources, such as snoring by the patient 1000 or background noise near the patient 1000.

According to an exemplary arrangement shown in FIG. 6B, a first microphone 5215-1 may be placed upstream of the reservoir 5110 to measure a reference noise, and a second microphone 5215-2 may be placed downstream of the reservoir 5110 to measure a resulting noise. The reference noise and resulting noise measurements may be correlated to a water quantity by, for example, calculating the attenuation in noise levels between the first microphone 5215-1 and the second microphone 5215-2. The attenuation in noise levels may be correlated to a quantity of water using similar methods to those described above (e.g., via a look-up table or a function).

Alternatively, in some forms, the reference noise may be estimated (e.g., according to another measure) rather than measured. In one example, where the reference noise includes a known noise output (e.g., from a component such as a speaker or a buzzer) the reference noise may be estimated as a predetermined noise. In some forms, the reference noise may be estimated based on another parameter such as motor speed or motor current. For example, a noise output of a RPT device 4000 and/or a humidifier 5000 or a component thereof (e.g., of the blower 4142) may be characterized by its manufacturer, from which a predetermined look-up table of reference noise may be saved onto a memory of the RPT device 4000 and/or a humidifier 5000.

In an arrangement shown in FIG. 9C, one or more measurements from a microphone 5215-3 may be used to determine the water quantity in the reservoir 5110. The microphone 5215-3 may produce a measurement of the resulting noise level $N_m3$, which may be used to determine the water quantity in this case using a look-up table or a function. In one example, a function may use as inputs the resulting noise level $N_m3$, as well as a predetermined reference noise to output (i.e., determine) the water quantity. In another example, a look-up table may be multi-dimensional, such that a look-up table may receive as inputs a motor speed, and the resulting noise level $N_m3$ to determine the water quantity.

Noise may be characterised in a number of ways, for example by a noise level (indicating amplitude, typically expressed in decibels or dB), as described above. Alternatively, or additionally, noise may be characterised by frequency domain data. For example, noise may be characterised such that for a noise level may be measured for one or more of a plurality of frequencies (or frequency bands). In the arrangement shown in FIG. 6B, a first noise spectrum may be determined at the first sensor 5215-1 and compared to a second noise spectrum determined at the second sensor 5215-2. Such a comparison may indicate how the first noise spectrum correlates to the second noise spectrum. For example, the comparison may evaluate changes in noise levels at a frequency and/or a frequency band in the first noise spectrum to the second noise spectrum. In one form, the first noise spectrum may be compared to a second noise spectrum, for example to determine a noise attenuation spectrum for correlation to a water quantity.

Measurements of noise may not be limited to those of audible frequency ranges. In some forms, measurements of inaudible vibrations of the flow of air, such as ultrasounds, may be used to determine a quantity of water in the reservoir 5110.

In another aspect of the present invention, a time lag between two locations in the pneumatic path may be used to determine the quantity of water. A change to the quantity of water in the reservoir 5110 may affect a length of time taken for the flow of air to travel through the humidifier reservoir 5110. Accordingly, the length of time taken, or the time lag, for the flow of air to travel through the humidifier reservoir 5110 may be correlated to the quantity of water in the reservoir 5110 by way of a look-up table or a function similarly to those described above.

FIG. 6 shows an exemplary arrangement of the present technology suitable for determining a time lag between two locations. In the arrangement shown in FIG. 6, the first sensor 5202-1 may determine a reference measure set, which may be a plurality (e.g., a series) of measurements or a single measure of the flow of air, where the reference measure is associated with a first time $T_1$ (e.g., a time at the start of the end of the reference measure). The second sensor 5202-2 may measure a resulting measure set associated with a second time $T_2$, wherein the resulting measure set correlates to the reference measure set. A difference in time ΔT may be determined (e.g., using an equation $\Delta T=T_2-T_1$) and may be correlated to the quantity of water. In some forms, where the resulting measure set and the reference measure set each comprise a waveform (e.g., a plurality of measurements made over a time period), the two waveforms may be compared for equivalence in the waveform shape to determine that the resulting measure correlates to the reference measure.

The determination of water quantity using any of the above methods may be made using a look-up table or a function. The particular look-up table and/or the function may vary between implementations of the present technology as the correlation may vary for a number of factors, for example locations of the sensor(s) or the geometry of the humidifier 5000. The number of variables used to create the look-up table and/or the function may be varied while taking advantage of the present technology. For example, as described above, introducing additional variables may improve the accuracy of the look-up table and/or the function, however in some forms, a look-up table or a function that uses one or two indicative characteristics as variables may be utilised.

It should be noted that the number of sensors employed towards determination of water quantity may be varied from the specific examples disclosed herewithin while still taking advantage of the present technology. In some cases, a pre-therapy and/or a post-therapy process may be executed by the controller to make the above measurements for detection of a correlated water quantity to determine water quantity by any of the methodologies described herein. However, in some cases such a process may be made periodically or continuously during a therapy session.

5.5.3.4.4 Measurements of the Humidifier 5000

According to another aspect of the present technology, the quantity of water in the reservoir 5110 may be determined from one or more measurements of characteristics of the humidifier 5000, such as its vibratory characteristics or mechanical characteristics.

5.5.3.4.4.1 Vibration

As the quantity of water in the reservoir 5110 varies, vibration characteristics of the reservoir 5110, and/or the humidifier 5000 may vary accordingly. For example, vibratory characteristics such as the damping ratio, natural frequencies and/or transmission loss of an object or a system (e.g., humidifier reservoir 5110 or humidifier 5000) may depend on one or more aspects of the object or the system, for example, the mass, density, material damping rate or stiffness among others. Further examples of vibration characteristics that may be affected include vibration attenuation through the humidifier reservoir 5110 (overall or depending on frequency), and natural vibration frequencies of the reservoir 5110. Thus one or more measurements of vibration characteristics (e.g., of the reservoir 5110 and/or the humidifier 5000) may be used to determine a quantity of water in the reservoir 5110, such as by correlating any of these characteristics with water quantities.

Vibration characteristics of the humidifier reservoir 5110 may be determined by one or more of a number of ways known to those skilled in the art. In one example, a measurement of vibration response may be compared against a vibration reference to determine vibration characteristics of the humidifier reservoir 5110.

According to one exemplary arrangement as shown in FIG. 10, a vibration source 5232 located on, for example, the RPT device 4000 and/or the humidifier 5000 may be configured to provide a reference vibration input such as a vibration impulse of a predetermined magnitude or a periodic vibration to the humidifier reservoir 5110. In some forms, a vibration source 5232 may provide a varying reference vibration input, for example where the blower 4142 is used as a vibration source 5232. A reference vibration from the blower 4142 may vary for example according to a pressure and/or flow rate delivered by the blower 4142. The reference vibration input may be, for example, in an audible frequency range, or an inaudible frequency range (i.e., subsonic or ultrasonic). The reference vibration input may also be predominantly transmitted to the reservoir 5110 via a gas, liquid, solid or any combination thereof, such as the flow of air, the water, or the structure of, for example, the RPT device 4000 and/or the humidifier 5000.

A vibration sensor 5234 as shown in FIG. 10 may be used to produce a measurement of a vibration response, for example of the humidifier reservoir 5110, including the water contained therein. A suitable example of a vibration sensor 5234 may be a piezoelectric accelerometer or a velocity sensor. The measurement of the vibration response may then be used to determine the quantity of water in the reservoir 5110. For instance, a natural frequency of the reservoir 5110 may typically increase as a quantity of water is reduced in the reservoir 5110, and may typically decrease as a quantity of water increases.

Alternatively, or additionally, a plurality of measurements of vibrations may be used to determine the quantity of water. For example, vibration may be measured at a plurality of locations, wherein the reservoir 5110 is located at least partially therebetween the two locations. A difference in the two measurements of vibration may be also referred to as vibration attenuation, and may depend on a quantity of water in the reservoir 5110. Thus a measurement of any number of vibration characteristics, such as the natural frequency of the reservoir, the overall magnitude of vibration at the reservoir 5110, or the vibration attenuation between the vibration reference and at the reservoir 5110 may also be used (e.g., by correlation) to determine the quantity of water.

As previously discussed, it may be preferable to arrange any sensors or sensors to be discrete from a disposable component such as the reservoir 5110. Therefore, in some forms, the vibration sensor 5234 may be removably coupled to the reservoir 5110 to measure its vibration characteristic (s), or measure vibration characteristic(s) of the reservoir 5110 indirectly. Thus, in one form, the vibration sensor 5234 may be configured to determine vibration characteristics of the reservoir 5110 such as by measuring a vibration response of the humidifier 5000.

5.5.3.4.4.2 Mechanical

In another aspect of the present technology, a mechanical property or a mechanical response of the humidifier 5000 and/or the reservoir 5110 may be measured to determine the quantity of water in the reservoir 5110.

According to one arrangement, a strain sensor/gauge (or a deformation sensor) may be placed at a base of the humidifier reservoir 5110 to measure a strain (or deformation) of a base of the reservoir 5110 due to the weight of the water therein, for example. The deformation of the base of the humidifier reservoir 5110 may be dependent on the quantity of water, thus the measurement of the deformation or strain may be correlated to determine to the quantity of water in the reservoir 5110. Alternatively, or additionally, the strain sensor may also be located at a number of other locations such as the side of the reservoir 5110, or on humidifier 5000 where it may be deformed according to a varying quantity of water in the reservoir 5110. Any number of other sensors such as tilt sensors or load cells may also produce a measurement that may be suitable indicative characteristics of the quantity of water. Yet further, similarly to above, a look-up table or a function may be used to determine the quantity of water from the measurement of the mechanical property produced by a sensor.

5.5.3.4.5 Measurements of Inertial Mass

According to another aspect of the present technology, the quantity of water in the reservoir 5110 may be determined by a measurement of an inertial mass of the water in the reservoir 5110. In one example, the inertial mass of the water in the reservoir 5110 may be determined by imparting a force to the water in the reservoir 5110 and measuring a response such as a resulting acceleration of the water or the reservoir 5110. The force may be imparted to the body of water in the reservoir 5110 in a number of ways, and a resulting acceleration of the water may be measured to determine to the inertial mass of the water.

In one example (see FIG. 12a), a reservoir 5110 may comprise a movable paddle 5112 that extends along a vertical direction of the reservoir 5110, and at least partially exposed to the flow of air. In one form, the paddle 5112 may be rotatably fixed to the reservoir 5110 about a paddle axis 5114 (e.g., vertical axis) within the reservoir 5110. The flow of air in the reservoir 5110 may act on exposed surface areas of the paddle 5112 to motivate the paddle 5112 to turn. Conversely, the quantity of water in the reservoir 5110 may resist a movement of the paddles 5112.

Furthermore, as the quantity of water in the reservoir 5110 changes, the area of the paddle 5112 exposed to the flow of air may change. This may have the effect of changing the force imparted into the paddle 5112 by the flow of air. At the same time, as the quantity of water changes, the resistance of the body of water to the paddles 5112 turning within the reservoir 5110 may also vary. Therefore, a measurement of movement of the paddle 5112 may be a suitable indicative characteristic from which the quantity of water may be inferred (e.g., correlated).

In another arrangement of the present technology, a sensor may be configured to determine measure of torque produced by the humidifier reservoir 5110. The flow of air may impart force and/or a torque to the reservoir 5110 as it travels therethrough. In some cases, the force and/or the torque imparted may be dependent on the quantity of water present in the reservoir 5110, as the internal volume of the reservoir 5110 that is exposed to the flow of air changes. For example, as the water quantity in the reservoir 5110 is reduced, the total surface area exposed to the flow of air may increase. Thus the measurement of torque may depend on the quantity of water in the humidifier reservoir 5110, and may be also a suitable indicative characteristic. The force and/or the torque may be measured by any number of sensors such as a load cell, force gauge, strain gauge or others known to those skilled in the art.

5.5.3.4.6 Movable Water Level Indicator

In one arrangement, the humidifier reservoir 5110 may comprise a movable portion configured to move as the quantity of water in the reservoir 5110 changes, for example by following the height of the quantity of water in the reservoir 5110. In one form, the movable portion may be a float located on the inside of the reservoir 5110, or it may be a part of the exterior of the reservoir 5110 such as a concertina section that is configured to move as the water level in the reservoir 5110 changes. The humidifier 5000 may comprise a sensor configured to determine the position or the height of the movable portion. The sensor may be, among others, an optical sensor configured to determine a position of the movable portion as shown in FIG. 11A, an angular sensor configured as shown in FIG. 11B to determine an angular position a pivotably coupled component configured to move with the movable portion, or a proximity sensor configured as shown in FIG. 11C to determine a distance between it and the humidifier movable portion.

According to the exemplary arrangement shown in FIG. 11A, the movable portion 5233 is coupled to the reservoir 5110 and configured to move according to a change in height of the water level (e.g., to be positioned at or near a top surface of the water). In FIG. 11A, where the top surface of the water is at a water level of WL-2, the movable portion 5233 may be positioned as shown, and for water levels of WL-1 or WL-3, the movable portion 5233 may be re-positioned accordingly. In this arrangement, the humidifier 5000 may comprise an optical sensor 5235 configured to determine the position of the movable portion 5233. In some forms, the optical sensor 5235 may comprise a field of view which spans positions of the movable portion 5233 for a maximum and a minimum allowable quantity of water, for example up to a first boundary of view 5235-1 and up to a second boundary of view 5235-2. The optical sensor 5235 may then produce a signal to indicate the position of the movable portion 5233 and/or the quantity of water in the reservoir 5110.

In another arrangement, shown in FIG. 11B, an angular sensor 5236 may be coupled to the movable portion 5233 using a connecting portion 5238. As the movable portion 5233 moves according to the quantity of water in the reservoir 5110, an angle α between the angular sensor 5236 and the connecting portion 5238 may be varied. The angular sensor 5236 may be configured to determine the angle α to produce a signal to indicate the position of the movable portion 5233 and/or the quantity of water in the reservoir 5110.

According to a yet another arrangement as shown in FIG. 11C, the humidifier 5000 may comprise a proximity sensor 5237 to determine a position of the movable portion 5233. In one example, the proximity sensor 5237 may be located toward the bottom of the humidifier 5000 and configured to detect proximity of the movable portion 5233. In such a configuration, as the movable portion 5233 moves according to the quantity of water in the reservoir 5110, the proximity sensor 5237 may produce a signal to indicate the position of the movable portion 5233 and/or the quantity of water in the reservoir 5110.

5.5.3.4.7 Electrical Properties

According to another aspect of the present technology, measurements of electrical properties of the body of water in the reservoir 5110 may be used to determine the quantity of water (e.g., by correlation). For example, capacitance and/or resistance of the volume of water may be measured by one or more sensors. The electrical properties of the body of water in the reservoir 5110 may vary according to the quantity of the body of water. For example, the capacitance of the water may increase as the quantity of the body of water is increased. Accordingly, electrical properties of the body of water in the reservoir 5110 may also be suitable indicative characteristics to be used to determine the quantity of water in the reservoir 5110.

5.5.3.4.8 Image Processing

A yet another aspect of the present technology may be use of image processing to determine the quantity of water in the reservoir 5110. According to one arrangement, the humidifier 5000 may comprise a camera configured to capture an image of the water in the reservoir 5110. The image may be processed by a controller such as the humidifier controller 5250, and analysed to identify features that could be used to determine the quantity of water (such as the water level).

In some cases, the captured image may be digitised, and then enhanced to accentuate features such as any boundaries such as an open surface of the water or boundaries between the water and the reservoir. Then the controller may execute image processing algorithms to extract and classify the features and any patterns so as to enable the quantity of water to be determined.

According to one arrangement of the present technology, the humidifier reservoir 5110 may be configured to enhance a distinction between water and air in the captured image, such as by improving a visual contrast between air, water and the reservoir for instance. In one instance, the reservoir may require a clear 'window' to allow the water to be clearly seen therethrough, or visual markers such as high-contrast surfaces or marked lines to improve identification of features by the image processing algorithm. Yet further, as the humidifier 5000 may often be in operation in a dark environment such as a bedroom during evening, the humidifier 5000 may comprise a lighting element to provide illumination to the reservoir 5110, the camera and/or the water.

5.5.3.4.9 Look-Up Tables or Functions

In any of above methods that may be used to determine, estimate, or infer, water quantity, it should be understood that one or more look-up tables, one or more functions, or a combination of any numbers both may be used to relate the measured characteristics to the quantity of water in the reservoir 5110 (e.g., correlation).

Yet further, it should be noted that indicative characteristics, or variables, that are used in the look-up tables or functions need not be measured directly by a sensor. An indicative characteristic may be determined or inferred from measurements of one or more other properties. For example, a flow rate of a gas may be inferred from other characteristics such as motor speed and electrical current, similarly to as disclosed in U.S. Pat. No. 6,237,593, the entire contents of which is included herewithin.

5.5.3.4.10 Learning/Calibration Mode

According to another aspect of the present technology, a humidifier 5000 may comprise an algorithm for a learning or calibration mode. A learning mode may modify, populate, or determine a look-up table and/or a function that correlates the one or more indicative characteristics with the water quantity.

For instance, in a learning mode, the controller may determine a rate at which water is consumed during a therapy session, for example until the reservoir 5110 is empty, or until the end of a session. Then, if appropriate, the controller may update the look-up table and/or the function based on the determined water consumption rates and measurements of the one or more relevant indicative characteristics. In one example, once the look-up table or function for a first indicative characteristic to be measured has been calibrated/correlated, the values for other indicative characteristics may be measured/determined and a correlation table/function therefore may be updated by the controller, based on the known accuracy of the previous look-up table or function for the first indicative characteristic.

Alternatively, the humidifier 5000 may comprise an algorithm for a calibration mode, which may be periodically triggered. In one exemplary arrangement of a calibration mode, a known, predetermined amount of water is entered into the humidifier reservoir 5110 and the controller tests how the look-up table or the function performs in determining the water quantity based on measurements of the indicative characteristics against the known, predetermined amount of water. One such test may be referred to as a calibration cycle. In some cases, a calibration mode may comprise multiple such calibration cycles for improved accuracy, in some cases with varying amounts of water. For example, the humidifier 5000 may instruct its user, such as the patient 1000 or the caregiver to fill the reservoir 5110 to a particular, known amount of water, to undertake calibration. Therefore use of such a calibration mode may improve accuracy of the look-up table and/or the function, and may also compensate for any inaccuracies that may develop in the system over its lifetime.

A calibration mode may be configured to run at a predetermined interval, such as every six months, and/or at a predetermined time or event, such as after a treatment period, during an initial set-up process of the humidifier 5000, during or after manufacturing or prior to sale of the humidifier 5000. In some instances, the calibration cycle may be performed by another party than the patient 1000, such as by a clinician, a caregiver or a home medical equipment provider. Alternatively, as described, it may be run during therapy in what may be a learn mode, or it may be arranged to prompt the user at a predetermined interval such as every month.

5.5.3.5 Humidity Delivery Algorithms

Another aspect of the present technology may relate to management of delivery of humidity to the flow of air, such as according to the quantity of water present in the humidifier reservoir 5110. For instance, a controller may ascertain an average length of a therapy session for the patient 1000 based on a predetermined typical length, or based on usage data of the patient 1000. Based on the determined average length of the therapy session, and the quantity of water determined to be present in the reservoir 5110, the controller may then determine a humidity profile to be delivered with the flow of air for the duration of the therapy session. In one example, the controller may determine a maximum output humidity that the patient 1000 may be able to set, so as to be able to deliver a humidified flow of air to the patient 1000 throughout a therapy session without running out of water.

According to another aspect, a rate of water usage may be determined based on one or more measurements of the quantity of water. For example, rates of water usage may be determined at various times throughout a therapy session by a controller. In some forms, the controller may determine a historical profile of water usage throughout the therapy session based on a plurality of measured rates of water usage. In one form, the controller may adjust one or more humidification settings based on the determined historical water usage profile. For example, if the water usage rate is above a threshold value (such as, for example, where the threshold value indicates a sustainable rate of consumption or maximum rate of consumption in reference to remaining time for an average or typical therapy session and a determined water quantity), the controller may reduce humidification output or a maximum humidifier output, and conversely the controller may increase humidification or a maximum humidifier output if the water usage rate is below a threshold value.

As illustrative examples, PCT patent application publication number WO/2006/015416 discloses, among others, methods of providing profiling delivery of humidified gas to a patient, potentially to improve breathing comfort or to maximise efficient use of water. US patent application publication number WO/2006/015416 discloses, among others, methods of providing humidity to a flow of air using a humidifier, controlling the absolute or relative humidity of the air to be provided to the patient. Materials disclosed in either application, by themselves or in combination with each other, may be suitable for use in combination with the present disclosure. The entire contents of both patent applications WO/2006/015416 and WO/2006/015416 are incorporated herein by reference.

5.6 Glossary

For the purposes of the present technology disclosure, in certain forms of the present technology, one or more of the following definitions may apply. In other forms of the present technology, alternative definitions may apply.

5.6.1 General

Air: In certain forms of the present technology, air may be taken to mean atmospheric air, and in other forms of the present technology air may be taken to mean some other combination of breathable gases, e.g., atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g., the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by a RPT device or emanating from a mask or patient interface. Ambient noise may be generated by sources outside the room.

Continuous Positive Airway Pressure (CPAP) therapy: CPAP therapy will be taken to mean the application of a supply of air to an entrance to the airways at a pressure that is continuously positive with respect to atmosphere. The pressure may be approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Patient: A person, whether or not they are suffering from a respiratory disease.

5.7 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.8 Reference Signs List

| Item | Reference |
| --- | --- |
| patient interface | 3000 |
| seal-forming structure | 3100 |
| plenum chamber | 3200 |
| positioning and stabilising structure | 3300 |
| vent | 3400 |
| decoupling structure | 3500 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| mechanical and pneumatic components | 4100 |
| air filter | 4110 |
| inlet air filter | 4112 |
| outlet air filter | 4114 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| supplemental oxygen | 4180 |
| electrical components | 4200 |
| PCBA | 4202 |
| power supply | 4210 |
| input device | 4220 |
| central controller | 4230 |
| clock | 4232 |
| therapy device controller | 4240 |
| protection circuit | 4250 |
| memory | 4260 |
| sensor | 4270 |
| pressure sensor | 4272 |
| flow rate sensor | 4274 |
| motor speed sensor | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| humidifier | 5000 |
| humidifier inlet | 5002 |
| humidifier outlet | 5004 |
| humidifier base | 5006 |
| humidifier reservoir | 5110 |
| paddle | 5112 |
| paddle axis | 5114 |
| reservoir inlet | 5118 |
| heating plate | 5120 |
| reservoir outlet | 5122 |
| reservoir dock | 5130 |
| locking lever | 5135 |
| water level reference | 5150 |
| conductive portion | 5152 |
| humidifier sensor | 5202 |
| pressure sensor | 5205 |
| flow rate sensor | 5210 |
| humidity sensor | 5218 |
| temperature sensor | 5220 |
| vibration source | 5232 |
| movable portion | 5233 |
| vibration sensor | 5234 |
| optical sensor | 5235 |
| angular sensor | 5236 |
| proximity sensor | 5237 |
| connecting portion | 5238 |
| heating element | 5240 |
| humidifier controller | 5250 |
| central humidifier controller | 5251 |
| heating element controller | 5252 |
| air circuit controller | 5254 |

The invention claimed is:

1. An apparatus for humidifying a flow of air to be delivered to a patient, the apparatus comprising:
   an inlet to receive the flow of air;
   an outlet to emit a humidified flow of air;
   a humidifier reservoir configured to contain a body of water for humidifying the flow of air, the humidifier reservoir being in fluid communication with the inlet and outlet;
   a humidifier base configured to receive the humidifier reservoir;
   a heating element disposed in the humidifier base proximate to a boundary of the humidifier reservoir to heat the body of water of the humidifier reservoir;
   a movable portion, the movable portion associated with the humidifier reservoir and configured to move in relation to the body of water;
   a sensor configured to generate a signal indicative of a plurality of positions of the movable portion ranging from a position corresponding to a maximum allowable reservoir water quantity level of the humidifier reservoir to a position corresponding to a minimum allowable reservoir water quantity level of the humidifier reservoir, wherein the sensor is disposed in the humidifier base with the heating element, and the sensor is in a fixed position near the boundary of the humidifier reservoir, wherein the sensor is positioned to sense, through the body of water and without contacting the moveable portion, positions of the plurality of positions of the moveable portion; and
   a controller configured to operate the heating element, the controller further configured to provide a reference regarding a reservoir water quantity of the humidifier reservoir based on the signal.

2. The apparatus of claim 1 wherein the sensor comprises a proximity sensor.

3. The apparatus of claim 1 wherein the movable portion is configured to be located inside the humidifier reservoir.

4. The apparatus of claim 1 wherein the controller is configured with one or more functions to determine the reservoir water quantity with one or more values from the signal.

5. The apparatus of claim 4 wherein the controller is configured to update a function of the one or more functions based on the determined reservoir water quantity.

6. The apparatus of claim 1 wherein the controller is configured with one or more look-up tables to determine the reservoir water quantity with one or more values from the signal.

7. The apparatus of claim 6 wherein the controller is configured to update a look-up table of the one or more look-up tables based on the determined reservoir water quantity.

8. The apparatus of claim 1 wherein the controller is configured to operate a calibration mode to sense a predetermined amount of water entered into the humidifier reservoir.

9. The apparatus of claim 1 wherein the controller is configured to determine a rate of water usage based on the signal.

10. The apparatus of claim 9 wherein the controller is configured to control an increase or decrease in humidification output based on the determined rate of water usage.

11. The apparatus of claim 1 wherein the controller is configured to determine a humidity profile to be delivered with the flow of air for a duration of a therapy session based on the reservoir water quantity.

12. The apparatus of claim 11 wherein the humidity profile comprises a maximum output humidity setting for the duration of the therapy session that permits humidification of the flow of air without running out of water.

13. The apparatus of claim 1 wherein the humidifier reservoir comprises a top and a bottom and the boundary is at the bottom of the humidifier reservoir, wherein the sensor comprises a proximity sensor positioned below the boundary and the movable portion and configured to detect a distance between the proximity sensor and the movable portion.

14. The apparatus of claim 1 wherein the movable portion comprises a float.

15. The apparatus of claim 1 wherein the movable portion is configured to float at a surface of the body of water.

16. The apparatus of claim 1 wherein the controller is configured to determine the reservoir water quantity of a plurality of different water levels based on the signal.

17. The apparatus of claim 1 wherein the reference comprises a percentage of a total volume of the humidifier reservoir.

18. The apparatus of claim 1 wherein the controller is configured to generate an alert or message concerning a reservoir water level condition based on a determined reservoir water quantity.

19. The apparatus of claim 18 further comprising a communications device, wherein the controller is configured to transmit the generated message with the communications device.

20. A system for humidifying a flow of air to be delivered to a patient, the system comprising:
an inlet means for receiving the flow of air;
an outlet means for emitting a humidified flow of air;
a reservoir means for containing a body of water for humidifying the flow of air, the reservoir means being in fluid communication with the inlet means and outlet means;
a receiving means for receiving the reservoir means;
a heating means disposed in the receiving means proximate to a boundary of the reservoir means for heating the body of water of the reservoir means;
a movable means, associated with the reservoir means, for moving in relation to the body of water;
sensing means for generating a signal indicative of a plurality of positions of the movable means ranging from a position corresponding to a maximum allowable reservoir water quantity level of the reservoir means to a position corresponding to a minimum allowable reservoir water quantity level of the reservoir means, wherein the sensing means is disposed in the receiving means with the heating means, and the sensing means is in a fixed position near the boundary of the reservoir means and the sensing means is positioned to sense, through the body of water and without contacting the moveable means, positions of the plurality of positions of the movable means; and
control means for operating the heating means, the control means further for providing a reference regarding a reservoir water quantity of the reservoir means based on the signal.

* * * * *